(12) United States Patent
Huang et al.

(10) Patent No.: US 7,888,380 B2
(45) Date of Patent: Feb. 15, 2011

(54) 1,2,4-TRIAZOLYLAMINOARYL (HETEROARYL) SULFONAMIDE DERIVATIVES

(75) Inventors: Shenlin Huang, Raritan, NJ (US); Ronghui Lin, East Brunswick, NJ (US); Peter J. Connolly, New Providence, NJ (US); Stuart L. Emanuel, Doylestown, PA (US); Steven A. Middleton, Flemington, NJ (US); Robert H. Gruninger, Easton, PA (US); Steven K. Wetter, Flemington, NJ (US)

(73) Assignee: Janssen Pharmaceutica, N.V., Beerse (BE)

( * ) Notice: Subject to any disclaimer, the term of this patent is extended or adjusted under 35 U.S.C. 154(b) by 1430 days.

(21) Appl. No.: 11/245,314

(22) Filed: Oct. 6, 2005

(65) Prior Publication Data

US 2006/0173020 A1    Aug. 3, 2006

Related U.S. Application Data

(60) Provisional application No. 60/617,119, filed on Oct. 8, 2004.

(51) Int. Cl.
| | | |
|---|---|---|
| *A61K 31/4196* | (2006.01) | |
| *A61K 31/496* | (2006.01) | |
| *A61K 33/42* | (2006.01) | |
| *C07D 249/14* | (2006.01) | |
| *C07D 257/04* | (2006.01) | |
| *C07F 9/572* | (2006.01) | |
| *C07F 9/6515* | (2006.01) | |
| *C07F 9/6518* | (2006.01) | |
| *C07F 9/6509* | (2006.01) | |

(52) U.S. Cl. .................. 514/381; 514/383; 514/255.05; 514/79; 514/93; 548/264.8; 548/251; 548/112; 544/337; 544/405

(58) Field of Classification Search ........................ None
See application file for complete search history.

(56) References Cited

U.S. PATENT DOCUMENTS

| | | | |
|---|---|---|---|
| 6,720,338 B2 | 4/2004 | Augeri et al. | |
| 6,924,302 B2* | 8/2005 | Lin et al. ................... | 514/383 |

FOREIGN PATENT DOCUMENTS

| | | | |
|---|---|---|---|
| WO | WO 99/32466 A1 | 7/1999 | |
| WO | WO 01/09106 A1 | 2/2001 | |
| WO | WO 02/057240 A1 | 7/2002 | |
| WO | WO 2004/046120 A2 | 6/2004 | |

OTHER PUBLICATIONS

Pardee A. et al; "Animal cell cycle", *Ann. Rev. Biochem.*, 1978, vol. 47, pp. 715-750.

Kishimoto T. et al, "In vivo regulation of the entry into M-phase: initial activation and nuclear translocation of cyclin B/Cdc2", *Prog. Cell Cycle Res.*, 1997, vol. 3, pp. 241-249.
Kato J. et al., "Induction of S phase by G1 regulatory factors", *Front. Bioscience*, 1991, vol. 4, pp. 787-792.
Kitagawa M. et al, "Phosphorylation of E2F-1 by cyclin A-cdk2", *Oncogene*, 1995, vol. 10, pp. 229-236.
DelSal G. et al., "Cell Cycle and Cancer: Critical Events and the G1 Restriction Point," *Critical Reviews in Oncogenesis*, 1996, vol. 71, pp. 127-142.
Loda M. et al., "Increased Proteasome-dependent Degradation of the Cyclin Dependent Kinase Inhibitor p27 in Aggressive Colorectal Carcinomas," *Nature Medicine*, 1997, vol. 3, pp. 231-234.
Nobori T. et al, "Deletions of the Cyclin Dependent Kinases 4 Inhibitor Gene in Multiple Human Cancers," 1994, *Nature*, vol. 368, pp. 753-756.
Kim J. et al., "Discovery of Aminothiazole Inhibitors of Cyclin Dependent Kinase 2: Synthesis, X-ray Crystallographic Analysis, and Biological Activities", *J. Med. Chem.*, 2002, vol. 45, pp. 3905-3927.
Thomas J. et al, "Phase I Clinical and Pharmacokinetic Trial of the Cyclin Dependent Kinase Inhibitor Flavopiridol", *Cancer Chemotherapy & Pharmacology*, 2002, vol. 50, pp. 465-472.
Kouroukis T. et al, "Flavopiridol in Untreated or Relapsed Mantle-cell Lymphoma: Results of a Phase II Study of the National Cancer Institute of Canada Clinical Trials Group", *Journal of Clinical Oncology*, 2003, vol. 21, pp. 1740-1745.
Schwartz G. et al., "Phase II Study of Cyclin Dependent Kinases Inhibitor Flavopiridol Administered to Patients with Advanced Gastric Carcinoma", *Journal of Clinical Oncology*, 2001, vol. 19, pp. 1985-1993.
Owa T. et al. "Discovery of Novel Antitumor Sulphonamides Targeting G1 Phase of the Cell Cycle", *J. Med. Chem.*, 1999, vol. 42, pp. 3789-3799.

(Continued)

*Primary Examiner*—Kamal A Saeed
*Assistant Examiner*—Michael Barker
(74) *Attorney, Agent, or Firm*—Patton Boggs LLP

(57) ABSTRACT

1,2,4-Triazolylaminoaryl(heteroaryl)sulfonamide derivatives of formula (I), pharmaceutically acceptable salts thereof, processes for the manufacture of 1,2,4-triazolylaminoaryl(heteroaryl)sulfonamide derivatives and pharmaceutical compositions containing 1,2,4-triazolylaminoaryl(heteroaryl)sulfonamide derivatives are disclosed:

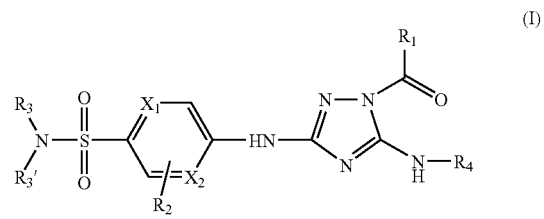

The 1,2,4-triazolylaminoaryl(heteroaryl)sulfonamide derivatives of formula (I) possess cell cycle inhibitory activity and are accordingly useful for their anti cell proliferation (such as anti cancer) activity.

27 Claims, No Drawings

OTHER PUBLICATIONS

Ozawa Y. at al., "E7070, A Novel Sulphonamide Agent With Potent Antitumor Activity in vitro and in vivo", *Eur. J. of Cancer*, 2001, vol. 37, pp. 275-282.

McClue S. et al., "In Vivo and In Vitro Antitumor Properties of The Cyclin Dependent Kinase Inhibitor CYC 202 (R-roscovitine)", *International Journal of Cancer*, 2002, vol. 102(5), pp. 463-468.

Senderowicz A.M. et al, "Phase I Trial of Infusion UCN-01, a Novel Protein Kinase Inhibitor, in Patients With Refractory Neoplasms", *Annals of Oncology*, 1998, vol. 9 (Suppl. 2), p. 111.

Macdonald, Donald L. 'Preparation of Glycosyl Phosphates. β—D—Fructopyranose 2-Phosphate' J. Org. Chem. Feb. 1966. 31(2) pp. 513-516.

International Search Report re: PCT/US05/36396 dated Mar. 7, 2006.

* cited by examiner

1,2,4-TRIAZOLYLAMINOARYL (HETEROARYL) SULFONAMIDE DERIVATIVES

CROSS REFERENCE TO RELATED APPLICATIONS

This present application claims benefit of U.S. Provisional Patent Application Ser. No. 60/617,119, filed Oct. 8, 2004, which is incorporated herein by reference in its entirety and for all purposes.

FIELD OF THE INVENTION

The invention is directed to 1,2,4-triazolylaminoaryl(heteroaryl)sulfonamide derivatives, or pharmaceutically acceptable salts which possess cell cycle inhibitory activity and are accordingly useful for their anti cell proliferation (such as anti cancer) activity. The invention is also directed to processes for the manufacture of said 1,2,4-triazolylaminoaryl(heteroaryl) sulfonamide derivatives, to pharmaceutical compositions containing them and to their use in the manufacture of medicaments or use in the generation of an anti cell proliferation effect.

BACKGROUND OF THE INVENTION

The cell division cycle is the fundamental biological process by which a cell grows, replicates its DNA and then divides to give two daughter cells. It includes four sequential phases, G1, S, G2, and M (see Pardee et al.; "Animal cell cycle", *Ann. Rev. Biochem.*, Vol. 47(1978), 715-750). DNA replication occurs in S phase, and replicated DNA is distributed to two genetically identical daughter cells in M phase. Between these two phases are gap1 (G1) and gap2 (G2). G1 is between M phase and S phase when a cell is responsive to extracellular stimuli and starting to grow. Gap2 is between S phase and M phase when the cell prepares for entry into mitosis. Lengths of the individual phases of the cell cycle can vary with cell type and with conditions. In addition, there is a fifth state known as G0 (or quiescence), into which cells may reversibly exit from the cell cycle but remain metabolically active.

The cell division cycle is regulated by the cyclin dependent kinases (CDKs), which belong to the family of serine/threonine kinases. For full activity, these kinases must form a complex with a member of the cyclin family of regulatory subunits and be phosphorylated on a specific threonine or serine residue (e.g., Thr 161 for cdk1). These active CDK/cyclin complexes then regulate cell cycle progression by phosphorylating their protein substrates whose activities are required at specific phases of the cell cycle. For example, in late S phase cyclin B is expressed and forms active CDK1/cyclin B complex, which is required for the entry of cells into M phase and considered as M phase promoting factor (see Kishimoto et al., "In vivo regulation of the entry into M-phase: initial activation and nuclear translocation of cyclin B/Cdc2", *Prog. Cell Cycle Res.*, Vol. 3 (1997), 241-249). This CDK1/cyclin B complex could phosphorylate several proteins including Histone H1, DNA polymerase alpha, RNA polymerase II, retinoblastoma tumor suppressor protein (Rb), lamin A, cAb1, nucleolin, which are involved in the early events of mitosis. In early G1, cyclin Ds are expressed and active CDK4/cyclin D and CDK6/cyclin D are formed, which then phosphorylate retinoblastoma tumor suppressor protein Rb (see Kato et al., "Induction of S phase by G1 regulatory factors", *Front. Biosci.*, Vol. 4 (1999), 787-792). In late G1, the cyclin Es are expressed and active CDK2/cyclin E complexes are generated, which also phosphorylate Rb. It is this sequential phosphorylation of Rb by CDK4/cyclin D, CDK6/cyclin D and CDK2/cyclin E that blocks its growth inhibitory effects. When Rb is hypophosphorylated, it tightly binds and blocks the activity of E2F, a trancription factor complex that is necessary for the expression of genes governing the G1 to S phase transition. When Rb is phosphorylated, its interaction with E2F is disrupted and E2F dependent transcription occurs. This allows the cell to pass the restriction point after which the cell no longer needs mitogenic stimulation to complete one cell cycle. In S phase, cyclin A(s) are expressed and active CDK2/cyclin A complexes are formed, which can phosphorylate the transcription factors B-Myb and E2F, and cdc6, a factor required for the initiation of DNA replication (see Kitagawa et al., "Phosphorylation of E2F-1 by cyclin A-cdk2", *Oncogene*, Vol. 10 (1995), 229-236). The sequential activation of CDK/cyclin complexes and their ability to phosphorylate and thus regulate the action of other proteins allows a cell to progress from one completed phase of the cell cycle to the next, in the correct order.

Disruption in the function of CDKs and the order of cell cycle is implicated in the hyperproliferative diseases, such as cancer, psoriasis and rheumatoid arthritis (Kamb et al., "A Cell Cycle Regulator Potentially Involved in Genesis of Many Tumor Types," *Science*, Vol. 264 (1994), 436-440).

For example, cyclin D1 is overexpressed in breast, esophageal, and squamous cell carcinomas (DelSal et al., "Cell Cycle and Cancer: Critical Events and the G1 Restriction Point," *Critical Rev. Oncogenesis*, Vol. 71 (1996), 127-142) and overexpression of cyclin E is linked to a wide variety of solid tumors. The expression of CDK inhibitor p27, which is a substrate and also inhibitor of CDK2/cyclin E, is normally inhibited in prostate, colon and breast cancers, and the cellular levels of p27 are inversely correlated with the stage of disease (see Loda et al., "Increased Proteasome-dependent Degradation of the Cyclin Dependent Kinase Inhibitor p27 in Aggressive Colorectal Carcinomas," *Nature Medicine*, Vol. 3 (1997), 231-234). In addition, genes encoding the CDK4 specific inhibitors of the p16 family frequently have deletions and mutations in sarcomas, leukemias, gliomas, familial melanoma and pancreatic, non-small cell lung, and head and neck carcinomas (see Nobori et al., "Deletions of the Cyclin Dependent Kinases 4 Inhibitor Gene in Multiple Human Cancers," *Nature*, Vol. 368 (1994), 753-756). These data clearly confirm the unregulation of CDKs activity in oncogenesis.

The emerging data provide strong evidence for using compounds inhibiting CDKs, CDK2, and CDK4 in particular, as antiproliferative therapeutic agents. For example, BMS 387032 (Bristol-Myers. Squibb) is currently in Phase I clinical trials as an oncology chemotherapeutic (see Kim et al., "Discovery of Aminothiazole Inhibitors of Cyclin Dependent Kinase 2: Synthesis, X-ray Crystallographic Analysis, and Biological Activities", *J. Med. Chem.*, Vol. 45 (2002), 3905-3927) and is a selective ATP competitive inhibitor for CDK2 ($IC_{50}$ of 48 nM). This compound induces cell cycle arrest and apoptosis, with concomitant inhibition of phosphorylation of CDK2 substrates such as retinoblastoma protein, demonstrating cytotoxicity in 40 human cell lines and showing antitumor activity in five tumor models, including P388 mouse leukemia, Cyclin E overexpressing transgenic mouse breast carcinoma, A2780 human ovarian carcinoma, Colo205 human colorectal carcinoma, and A431 human squamous cell carcinoma. Likewise, flavopiridol has shown potent activity against CDKs, arresting the cell cycle in the G1 and G2 phases by direct inhibition of CDK2, CDK4, and CDK1 and by down regulation of cyclins D1, D3, and B, inhibiting various human cancer cell lines and showing activity in prostate melanoma, breast cancer and NSCLC tumor xenograft models. Flavopiridol was administered by IV infusion to patients with advanced tumors in a Phase I study (see Thomas et al., "Phase I Clinical and Pharmacokinetic Trial of the Cyclin Dependent Kinase Inhibitor Flavopiridol", *Cancer Chemotherapy & Pharmacology*, Vol. 50 (2002), 465-72). A partial response was observed in a patient with renal cancer and 3 minor responses were seen in one of each patients with colon or prostate cancer and non-hodgkin's lymphoma. A phase II trial investigated the use of flavopiridol and paclitaxel with or without co-administration of cisplatin in the treatment of 54 patients with advanced solid tumors. Among the 51 evaluable patients, a total of 1 complete, 1 partial and 1 minor response and 21 cases of stable disease were reported (see Koroukis et al., "Flavopiridol in Untreated or Relapsed Mantle-cell Lymphoma: Results of a Phase II Study of the National Cancer Institute of Canada Clinical Trials Group", *Journal of Clinical Oncology*, Vol. 21 (2003), 1740-45; and Schwartz et al., "Phase II Study of Cyclin Dependent Kinases Inhibitor Flavopiridol Administered to Patients with Advanced Gastric Carcinoma", *Journal of Clinical Oncology*, Vol. 19 (2001), 1985-93). Indisulam (E-7070) is a novel sulfonamide agent in Phase II with Eisai for head and neck cancer, solid tumor, CRC and NSLC and has demonstrated a unique antitumor spectrum in vitro and excellent antitumor activity in vivo affecting multiple cell-cycle checkpoints. E-7070 suppresses the expression of cyclin E and phosphorylation of CDK2 by blocking cell cycle progression at several points, including G1/S and G2/M transition. In vivo studies showed its activity against various human cancers, such as colon carcinomas HCT116, LS174T, SW620 and HCT15 and NSCLC PC-9 (see Ova et al. "Discovery of Novel Antitumor Sulphonamides Targeting G1 Phase of the Cell Cycle", *J. Med. Chem.*, Vol. 42 (1999), 3789-3799; and Ozawa et al., "E7070, A Novel Sulphonamide Agent With Potent Antitumor Activity in vitro and in vivo", *Eur. J. of Cancer*, Vol. 37 (2001), 275-282). Roscovitine (Cyc 202) (Cyclacel) is in clinical development for various cancers, inhibiting CDK2 and to a lesser extent also CDK1. This compound is cytotoxic in HCT116 human colon carcinoma cells and has been shown in patients to induce apoptosis by acting on G1/S or early checkpoint (see McClue et al., "In Vivo and In Vitro Antitumor Properties of The Cyclin Dependent Kinase Inhibitor CYC 202 (R-roscovitine)", *International Journal of Cancer*, Vol. 102(5) (2002), 463-468). UCN-01 (Kyowa Hakko Kogyo) is a non-specific kinase inhibitor with activity against PKCs and CDKs. Preclinical data indicates that the main potential of UCN-01 is in the treatment of leukemias, in particular CLL, but the compound has been advanced clinically in renal cell carcinoma and pancreatic cancer. Furthermore, this compound has shown antitumor activity in patients with melanoma and lymphoma (see Senderowicz et al., "Phase I Trial of Infusion UCN-01, a Novel Protein Kinase Inhibitor, in Patients With Refractory Neoplasms", *Annals of Oncology*, Vol. 9 (Suppl. 2) (1998), 111).

WO200109106 discloses diamino-1,2,4-triazole-carboxylics and their use in the treatment of conditions associated with a need for inhibition of GSK-3.

WO2002057240 discloses substituted triazole diamine derivatives and their use as inhibitors of protein kinases.

WO2004046120 discloses diaminotriazoles and their use as inhibitors of protein kinases.

However, the demand is still increasing for small molecule compounds that can be readily made and are potent inhibitors of one or more CDKs or CDK/cyclin complexes. Because CDK1 may serve as an M phase promoting factor and govern the G2 phase of the cell cycle, and CDK2/cyclin E controls the early G1 phase of the cell cycle, there is a need for effective and specific inhibitors of CDK1 and/or CDK2 for treating one of more types of tumors.

Also, inhibition of CDKs may prevent progression in the cell cycle in normal cells and limit the toxicity of cytotoxics which act in S phase, G2 or Mitosis. Such disruption of the cell cycle or normal proliferating cells should therefore protect proliferating cells such as hair follicles and epithelial mucosa from the effects of cytotoxic agents and thereby provide a potent treatment for side effects associated with cancer chemo- and radiotherapies.

BRIEF SUMMARY OF THE INVENTION

The present invention is based on the discovery that certain 1,2,4-triazolylaminoaryl(heteroaryl)sulfonamide compounds inhibit the effects of cell cycle kinases, showing selectivity for CDK1 and CDK2, and thus possessing antitumor activity including (anti cell proliferation\migration and\or apoptotic) properties.

These properties could be used for the treatment of a CDK mediated disease manifested by abnormal cell cycle control such as cancers (solid tumors and leukemias), fibroproliferative and differentiative disorders, psoriasis, acute and chronic nephropathies, rheumatoid arthritis, Kaposi's sarcoma, hemangioma atheroma, atherosclerosis, arterial restenosis, autoimmune disease, acute and chronic inflammation, bone diseases and ocular diseases with retinal vessel proliferation.

Accordingly, the present invention provides a 1,2,4-triazoloaminoaryl(heteroaryl)sulfonamide derivative of formula (I):

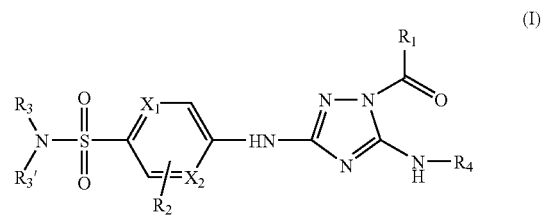

wherein:

$X_1$, $X_2$ are independently selected from CH and N, $R_1$ is a carbocyclic, heterocyclic or heteroaryl, wherein $R_1$ is optionally substituted with one or more substitutents independently selected from amido, phosphonato, phosphine, carboxyl, thiocarbonyl, sulfonyl, nitro, thiol, thioether, amine, cyano, N—($C_{1-6}$-alkyl)amino, N,N—($C_{1-6}$-alkyl)$_2$amino, sulfonamide, ketone, aldehyde, ester, halogen, oxygen, haloalkyl, $C_{1-6}$-alkyl, $C_{2-6}$-alkenyl, $C_{2-6}$-alkynyl, hydroxyl, or $C_{1-6}$-alkoxyl, $R_2$ is hydrogen, hydroxy, nitro, amino, carboxy, carbamoyl, halo, cyano, trifluoromethyl, trifluoromethoxy, sulphamoyl, mercapto, $C_{1-6}$-alkyl, $C_{2-6}$-alkenyl, $C_{2-6}$-alkynyl, $C_{1-6}$-alkoxyl, N—($C_{1-6}$-alkyl)amino, N,N—($C_{1-6}$-alkyl)$_2$amino, or sulfonyl, $R_3$ and $R_4$ are independently selected from hydrogen, —$CH_2OPO_3R_5R_6$, —$CH_2OCOR_7$, —$CH_2OCO_2R_7$, —$CH_2OCONHR_7$, —$COR_7$, or —$CONHR_7$, wherein $R_3$ and $R_4$ are not simultaneously hydrogen, $R_3'$ is selected from the group consisting of hydrogen, heterocyclic or $C_{1-8}$alkyl, wherein $C_{1-8}$alkyl is optionally substituted with one or more of —$CO_2H$, —$CO_2(C_{1-6})$alkyl, hydroxy, $C_{1-6}$alkoxy, amino, aminoacylamino, N—($C_{1-6}$-alkyl)amino, N,N—($C_{1-6}$alkyl)$_2$amino, heterocyclic or heteroaryl, $R_5$ and $R_6$ are each selected from hydrogen, $C_{1-6}$alkyl, Na, K and NH$_4$ and are the same unless either $R_5$ or $R_6$ is absent, hydrogen or $C_{1-6}$alkyl, in which case the other is different, or alternatively, $R_5$ and $R_6$ together represent calcium, or magnesium, $R_7$ is heterocyclic or $C_{1-6}$alkyl, wherein $C_{1-6}$alkyl is optionally substituted with one or more of —CO$_2$H, —CO$_2$($C_{1-6}$) alkyl, amino, amino-COR$_8$, carbamoyl, carbamoyl($C_{1-6}$) alkyl, guanidino, mercapto, thio($C_{1-6}$)alkyl, hydroxy, N—($C_{1-6}$-alkyl)amino, N,N—($C_{1-6}$-alkyl)$_2$amino, aryl optionally substituted on aryl with one or more of $C_{1-4}$alkyl, $C_{1-4}$alkoxy, hydroxy, halogen, amino, aminoalkyl, nitro or cyano, heterocyclic, —(OCH$_2$CH$_2$)$_n$OCH$_3$ where n is 0-400, —(OCH$_2$CH$_2$)$_n$OH where n is 0-400, or —(OCH$_2$CH$_2$)$_n$OCH$_2$CO$_2$H where n is 0-400, and $R_8$ is $C_{1-6}$alkyl optionally substituted with one or more of —CO$_2$H, —CO$_2$($C_{1-6}$)alkyl, amino, aminoacylamino, carbamoyl, carbamoyl($C_{1-6}$)alkyl, guanidino, mercapto, thio($C_{1-6}$)alkyl, hydroxy, N—($C_{1-6}$-alkyl)amino, N,N—($C_{1-6}$-alkyl)$_2$amino, aryl optionally substituted on aryl with one or more of $C_{1-4}$alkyl, $C_{1-4}$alkoxy, hydroxy, halogen, amino, aminoalkyl, nitro or cyano, heterocyclic, —(OCH$_2$CH$_2$)$_n$OCH$_3$ where n is 0-400, —(OCH$_2$CH$_2$)$_n$OH where n is 0-400, or —(OCH$_2$CH$_2$)$_n$OCH$_2$CO$_2$H where n is 0-400.

An example of a compound of formula (I) includes compounds wherein $X_1$ and $X_2$ is each CH.

An example of a compound of formula (I) includes compounds wherein $R_1$ is a carbocyclic compound selected from cyclopropyl, cyclobutyl, cyclopentyl, cyclohexyl, phenyl or naphthyl each optionally substituted with one or more of amido, phosphonato, phosphine, carboxyl, thiocarbonyl, sulfonyl, nitro, thiol, thioether, amine, cyano, N—($C_{1-6}$-alkyl)amino, N,N—($C_{1-6}$-alkyl)$_2$amino, sulfonamide, ketone, aldehyde, ester, halogen, oxygen, haloalkyl, $C_{1-6}$-alkyl, $C_{2-6}$-alkenyl, $C_{2-6}$-alkynyl, hydroxyl or $C_{1-6}$-alkoxyl.

An example of a compound of formula (I) includes compounds wherein $R_1$ is phenyl optionally substituted with one or more of amido, phosphonato, phosphine, carboxyl, thiocarbonyl, sulfonyl, nitro, thiol, thioether, amine, cyano, N—($C_{1-6}$-alkyl)amino, N,N—($C_{1-6}$-alkyl)$_2$amino, sulfonamide, ketone, aldehyde, ester, halogen, oxygen, haloalkyl, $C_{1-6}$-alkyl, $C_{2-6}$-alkenyl, $C_{2-6}$-alkynyl, hydroxyl or $C_{1-6}$-alkoxyl.

An example of a compound of formula (I) includes compounds wherein $R_1$ is phenyl optionally substituted with one or more of halogen.

An example of a compound of formula (I) includes compounds wherein $R_1$ is a heterocyclic compound selected from pyrrolidinyl, piperidinyl or piperazinyl each optionally substituted with one or more of amido, phosphonato, phosphine, carboxyl, thiocarbonyl, sulfonyl, nitro, thiol, thioether, amine, cyano, N—($C_{1-6}$-alkyl)amino, N,N—($C_{1-6}$-alkyl)$_2$amino, sulfonamide, ketone, aldehyde, ester, halogen, oxygen, haloalkyl, $C_{1-6}$-alkyl, $C_{2-6}$-alkenyl, $C_{2-6}$-alkynyl, hydroxyl or $C_{1-6}$-alkoxyl.

An example of a compound of formula (I) includes compounds wherein $R_1$ is a heteroaryl compound selected from pyrazolyl, pyridinyl, pyrazinyl, pyridazinyl, pyrimidinyl, morpholinyl, thiazinyl, oxazinyl, pyrrolyl, indolyl, furanyl, thiophenyl, imidazolyl, oxazolyl, isoxazolyl, thiazolyl, triazolyl, tetrazolyl, quinolinyl, isoquinolinyl, quinazolinyl, acridinyl, benzimidazolyl, benzothiophenyl or benzofuranyl each optionally substituted with one or more of amido, phosphonato, phosphine, carboxyl, thiocarbonyl, sulfonyl, nitro, thiol, thioether, amine, cyano, N—($C_{1-6}$-alkyl)amino, N,N—($C_{1-6}$-alkyl)$_2$amino, sulfonamide, ketone, aldehyde, ester, halogen, oxygen, haloalkyl, $C_{1-6}$-alkyl, $C_{2-6}$-alkenyl, $C_{2-6}$-alkynyl, hydroxyl or $C_{1-6}$-alkoxyl.

An example of a compound of formula (I) includes compounds wherein $R_2$ is hydrogen.

An example of a compound of formula (I) includes compounds wherein $R_3$ and $R_4$ are independently selected from hydrogen or —COR$_7$, wherein $R_3$ and $R_4$ are not simultaneously hydrogen.

An example of a compound of formula (I) includes compounds wherein $R_3'$ is a heterocyclic compound selected from morpholinyl, tetrazolyl, pyrrolidinyl, piperidinyl, piperazinyl or 4-methyl-piperazin-1-yl.

An example of a compound of formula (I) includes compounds wherein $R_3'$ is a heteroaryl compound selected from imidazolyl, 2-methyl-imidazolyl, 2,3-dimethyl-imidazolyl, 1,2,3-triazolyl or 1,2,4-triazolyl.

An example of a compound of formula (I) includes compounds wherein $R_3'$ is hydrogen.

An example of a compound of formula (I) includes compounds wherein $R_7$ is a heterocyclic compound selected from morpholinyl, tetrazolyl, pyrrolidinyl, piperidinyl, piperazinyl or 4-methyl-piperazin-1-yl.

An example of a compound of formula (I) includes compounds wherein $R_7$ is heterocyclic or $C_{1-6}$alkyl, wherein $C_{1-6}$alkyl is optionally substituted with one or more of —CO$_2$H, —CO$_2$($C_{1-6}$)alkyl, amino, amino-COR$_8$, carbamoyl, carbamoyl($C_{1-6}$)alkyl, guanidino, mercapto, thio($C_{1-6}$) alkyl, hydroxy, N,N—($C_{1-6}$-alkyl)$_2$amino, phenyl optionally substituted on phenyl with one or more of $C_{1-4}$alkyl, $C_{1-4}$alkoxy, hydroxy, halogen, amino, aminoalkyl, nitro or cyano, heterocyclic, —(OCH$_2$CH$_2$)$_n$OCH$_3$ where n is 0, 1, 2 or 3, —(OCH$_2$CH$_2$)$_n$OH where n is 0, 1, 2 or 3, or —(OCH$_2$CH$_2$)$_n$OCH$_2$CO$_2$H where n is 0, 1, 2 or 3.

An example of a compound of formula (I) includes compounds wherein $R_7$ is heterocyclic or $C_{1-6}$alkyl, wherein $C_{1-6}$alkyl is optionally substituted with one or more of —CO$_2$H, —CO$_2$($C_{1-6}$)alkyl, amino, amino-COR$_8$, carbamoyl, carbamoyl($C_{1-6}$)alkyl, guanidino, mercapto, thio($C_{1-6}$) alkyl, hydroxy, N,N—($C_{1-6}$-alkyl)$_2$amino, phenyl optionally substituted on phenyl with one or more of hydroxy, heterocyclic, —(OCH$_2$CH$_2$)$_n$OCH$_3$ where n is 1 or 2 or —(OCH$_2$CH$_2$)$_n$OCH$_2$CO$_2$H where n is 1 or 2.

An example of a compound of formula (I) includes compounds wherein $R_7$ is heterocyclic or $C_{1-6}$alkyl, wherein $C_{1-6}$alkyl is optionally substituted with one or more of —CO$_2$H, —CO$_2$($C_{1-6}$)alkyl, amino, amino-COR$_8$, hydroxy, N,N—($C_{1-6}$-alkyl)$_2$amino, heterocyclic, —(OCH$_2$CH$_2$)$_n$OCH$_3$ where n is 1 or 2 or —(OCH$_2$CH$_2$)$_n$OCH$_2$CO$_2$H where n is 1 or 2.

An example of a compound of formula (I) includes compounds wherein $R_8$ is $C_{1-6}$alkyl optionally substituted with one or more of —CO$_2$H, —CO$_2$($C_{1-6}$)alkyl, amino, hydroxy, N—($C_{1-6}$-alkyl)amino, N,N—($C_{1-6}$-alkyl)$_2$amino, aryl optionally substituted on aryl with one or more of $C_{1-4}$alkyl, $C_{1-4}$alkoxy, hydroxy, halogen, amino or aminoalkyl, heterocyclic, —(OCH$_2$CH$_2$)$_n$OCH$_3$ where n is 0, 1, 2 or 3, —(OCH$_2$CH$_2$)$_n$OH where n is 0, 1, 2 or 3, or —(OCH$_2$CH$_2$)$_n$OCH$_2$CO$_2$H where n is 0, 1, 2 or 3.

An example of a compound of formula (I) includes compounds wherein $R_8$ is $C_{1-6}$alkyl optionally substituted with one or more of amino.

In a second aspect of this invention, there is provided a compound of formula (II):

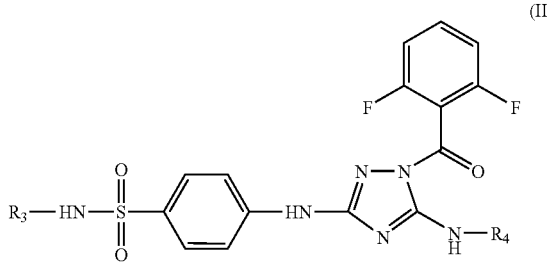

(II)

wherein:

$R_3$ and $R_4$ are independently selected from hydrogen, —$CH_2OPO_3R_5R_6$, —$CH_2OCOR_7$, —$CH_2OCO_2R_7$, —$CH_2OCONHR_7$, —$COR_7$, or —$CONHR_7$, wherein $R_3$ and $R_4$ are not simultaneously hydrogen, $R_5$ and $R_6$ are each selected from hydrogen, $C_{1-6}$alkyl, Na, K and $NH_4$ and are the same unless either $R_5$ or $R_6$ is absent, hydrogen or $C_{1-6}$alkyl, in which case the other is different, or alternatively, $R_5$ and $R_6$ together represent calcium, or magnesium, and $R_7$ is heterocyclic or $C_{1-6}$alkyl, wherein $C_{1-6}$alkyl is optionally substituted with one or more of —$CO_2H$, —$CO_2(C_{1-6})$alkyl, amino, amino-$COR_8$, carbamoyl, carbamoyl($C_{1-6}$)alkyl, guanidino, mercapto, thio($C_{1-6}$)alkyl, hydroxy, N—($C_{1-6}$-alkyl)amino, N,N—($C_{1-6}$-alkyl)$_2$amino, aryl optionally substituted on aryl with one or more of $C_{1-4}$alkyl, $C_{1-4}$alkoxy, hydroxy, halogen, amino, aminoalkyl, nitro or cyano, heterocyclic, —$(OCH_2CH_2)_nOCH_3$ where n is 0-400, —$(OCH_2CH_2)_n$ OH where n is 0-400, or —$(OCH_2CH_2)_n$ $OCH_2CO_2H$ where n is 0-400, and $R_8$ is $C_{1-6}$alkyl optionally substituted with one or more of —$CO_2H$, —$CO_2(C_{1-6})$alkyl, amino, aminoacylamino, carbamoyl, carbamoyl($C_{1-6}$)alkyl, guanidino, mercapto, thio ($C_{1-6}$)alkyl, hydroxy, N—($C_{1-6}$-alkyl)amino, N,N—($C_{1-6}$-alkyl)$_2$amino, aryl optionally substituted on aryl with one or more of $C_{1-4}$alkyl, $C_{1-4}$alkoxy, hydroxy, halogen, amino, aminoalkyl, nitro or cyano, heterocyclic, —$(OCH_2CH_2)_nOCH_3$ where n is 0-400, —$(OCH_2CH_2)_nOH$ where n is 0-400, or —$(OCH_2CH_2)_nOCH_2CO_2H$ where n is 0-400.

In a third aspect of this invention, there is provided a compound of formula (III):

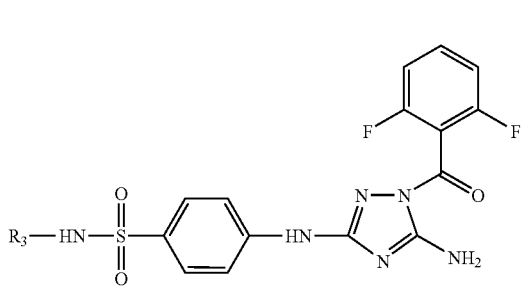

(III)

wherein:

$R_3$ is —$COR_7$, $R_7$ is heterocyclic or $C_{1-6}$alkyl, wherein $C_{1-6}$alkyl is optionally substituted with one or more of —$CO_2H$, —$CO_2(C_{1-6})$ alkyl, amino, amino-$COR_8$, carbamoyl, carbamoyl($C_{1-6}$) alkyl, guanidino, mercapto, thio($C_{1-6}$)alkyl, hydroxy, N—($C_{1-6}$-alkyl)amino, N,N—($C_{1-6}$-alkyl)$_2$amino, aryl optionally substituted on aryl with one or more of $C_{1-4}$alkyl, $C_{1-4}$alkoxy, hydroxy, halogen, amino, aminoalkyl, nitro or cyano, heterocyclic, —$(OCH_2CH_2)_nOCH_3$ where n is 0-400, —$(OCH_2CH_2)_nOH$ where n is 0-400, or —$(OCH_2CH_2)_n$ $OCH_2CO_2H$ where n is 0-400, and $R_8$ is $C_{1-6}$alkyl optionally substituted with one or more of —$CO_2H$, —$CO_2(C_{1-6})$alkyl, amino, aminoacylamino, carbamoyl, carbamoyl($C_{1-6}$)alkyl, guanidino, mercapto, thio ($C_{1-6}$)alkyl, hydroxy, N—($C_{1-6}$-alkyl)amino, N,N—($C_{1-6}$-alkyl)$_2$amino, aryl optionally substituted on aryl with one or more of $C_{1-4}$alkyl, $C_{1-4}$alkoxy, hydroxy, halogen, amino, aminoalkyl, nitro or cyano, heterocyclic, —$(OCH_2CH_2)_nOCH_3$ where n is 0-400, —$(OCH_2CH_2)_nOH$ where n is 0-400, or —$(OCH_2CH_2)_nOCH_2CO_2H$ where n is 0-400.

Accordingly, there is also provided, a pharmaceutical composition containing a compound of the formula (I), (II) or (III), or a pharmaceutically acceptable salt of a compound of the formula (I), (II) or (III); or a pharmaceutically active metabolite of a compound of the formula (I), (II) or (III), or a pharmaceutically acceptable salt of the metabolite, and the therapeutic use of the composition in treating or preventing kinase mediated diseases resulting from cellular hyperproliferation, such as cancer, rheumatoid arthritis and psoriasis.

The present invention provides a method for using compounds of Formula (I) in treating or ameliorating a kinase receptor-mediated disorder.

An aspect of the method includes inhibiting unregulated kinase activity comprising contacting the kinase domain with one or more compounds of Formula (I).

An aspect of the method includes inhibiting a kinase by contacting the kinase receptor with a compound of Formula (I).

An aspect of the method includes inhibiting increased or unregulated kinase expression or signaling leading to unregulated cell proliferation comprising contacting a kinase receptor with one or more compounds of Formula (I).

An aspect of the method includes inhibiting a cyclin dependent kinase by contacting the kinase receptor with a compound of Formula (I).

An aspect of the method includes inhibiting the unregulated expression of a cyclin dependent kinase and the like.

The present invention is also directed to a method for treating or preventing a kinase mediated disease in a subject in need thereof comprising administering to the subject an effective amount of said compound.

The present invention is further directed to a method for treating or preventing a cyclin dependent kinase mediated disease in a subject in need thereof comprising administering to the subject an effective amount of said compound.

The method further comprises administering to the subject an effective amount of a compound of formula (I), (II) or (III) or a pharmaceutically acceptable salt, active metabolite, salt of the metabolite or composition thereof in the form of a medicament.

Several other aspects, features and advantages of the invention will become apparent from the detailed description below.

DETAILED DESCRIPTION OF THE INVENTION

As used herein, the term "effective amount" means that amount of a drug or pharmaceutical agent that will result in improved healing, prevention, or treatment, or a decrease in the rate of advancement of a disease or disorder or the amelioration of disease, disorder, or side effect. The term also indicates the amount that could effectively enhance physiological function.

As used herein, the term "alkyl" means a straight or branched hydrocarbon chain having 1-8 carbon atoms, optionally substituted with lower alkyl, lower haloalkyl, lower alkylsufanyl, lower alkylsulfenyl, lower alkylsulfonyl, lower alkoxy, oxo, nitro, mercapto, amino optionally substituted by alkyl, carboxy, carbamoyl optionally substituted by alkyl, carboxamide optionally substituted by alkyl, aminosulfonyl optionally substituted by alkyl. Examples of "alkyl" as used herein include, but are not limited to, methyl, ethyl, propyl, n-butyl, n-pentyl, isobutyl, isopropyl and the like.

As used herein, the term "alkenyl" means a straight or branched hydrocarbon chain having 2-8 carbon atoms and at least one carbon-carbon double bond, optionally substituted with lower alkyl, lower haloalkyl, lower alkylsufanyl, lower alkylsulfenyl, lower alkylsulfonyl, lower alkoxy, oxo, nitro, mercapto, amino optionally substituted by alkyl, carboxy, carbamoyl optionally substituted by alkyl, carboxamide optionally substituted by alkyl, aminosulfonyl optionally substituted by alkyl. Examples of "alkenyl" as used herein include, but are not limited to, 1-propenyl, 1-butenyl, 1-pentenyl, and 1-hexenyl and the like.

As used herein, the term "alkynyl" means a straight or branched hydrocarbon chain having 2-8 carbon atoms and one carbon-carbon triple bond, optionally substituted with lower alkyl, lower haloalkyl, lower alkylsufanyl, lower alkylsulfenyl, lower alkylsulfonyl, lower alkoxy, oxo, nitro, mercapto, amino optionally substituted by alkyl, carboxy, carbamoyl optionally substituted by alkyl, carboxamide optionally substituted by alkyl, aminosulfonyl optionally substituted by alkyl. Examples of "alkynyl" as used herein include, but are not limited to, 1-propynyl, 1-butynyl, 2-butynyl, 1-pentynyl, and 1-hexynyl and the like.

The term "alkoxy" or "alkoxyl" means a straight or branched hydrocarbon chain having 1-8 carbon atoms attached via an oxygen linking atom and optionally substituted with lower alkyl, lower haloalkyl, lower alkylsufanyl, lower alkylsulfenyl, lower alkylsulfonyl, lower alkoxy, oxo, nitro, mercapto, amino optionally substituted by alkyl, carboxy, carbamoyl optionally substituted by alkyl, carboxamide optionally substituted by alkyl, aminosulfonyl optionally substituted by alkyl. Examples of "alkoxy" as used herein include, but are not limited to, methoxy, ethoxy, propoxy, butoxy and isopropoxy and the like.

As used herein, the term "carbocyclic" refers to a cycloalkyl or aryl ring.

As used herein, the term "cycloalkyl" refers to a saturated cyclic hydrocarbon ring having 3-10 carbons. Examples of "cycloalkyl" used herein include, but are not limited to, cyclopropyl, cyclobutyl, cyclopentyl and cyclohexyl and the like.

As used herein, the term "heterocyclyl" or "heterocyclic" refers to a 3-12 membered saturated or partially saturated ring containing one or more heteroatoms selected from S, SO, $SO_2$, O or N, said ring optionally substituted with lower alkyl, lower haloalkyl, lower alkylsufanyl, lower alkylsulfenyl, lower alkylsulfonyl, lower alkoxy, oxo, nitro, mercapto, amino optionally substituted by alkyl, carboxy, carbamoyl optionally substituted by alkyl, carboxamide optionally substituted by alkyl, aminosulfonyl optionally substituted by alkyl. Such a ring may be optionally fused to one or more other heterocyclyl, cycloalkyl, heteroaryl, or aryl rings. Examples of heterocyclyl include, but are not limited to, 2H-pyrrole (including 2-pyrrolinyl or 3-pyrrolinyl), 2-imidazolinyl (also referred to as 4,5-dihydro-1H-imidazolyl), imidazolidinyl, 2-pyrazolinyl, pyrazolidinyl, tetrazolinyl, tetrazolidinyl, piperidinyl, pyrrolidinyl, 1,4-dithianyl, thiomorpholinyl, piperazinyl, 4-methyl-1-piperazinyl, 2-pyrrolidinone, azetidinyl, azepanyl, hexahydro-1,4-diazepinyl, hexahydro-1,4-oxazepanyl, tetrahydro-furanyl, pyranyl, 1,4-dioxanyl, 1,3-dioxolanyl, tetrahydro-pyranyl, tetrahydro-pyridazinyl, 1,3-benzodioxolyl, 2,3-dihydro-1,4-benzodioxinyl, morpholinyl, 4-morpholinyl propyl, tetrahydrothiopyranyl, and tetrahydrothiophenyl and the like.

As used herein, the term "aryl" refers to an optionally substituted benzene ring or an optionally substituted benzene ring system fused to one or more optionally substituted benzene rings. The optional substituents include lower alkyl, lower haloalkyl, lower alkylsufanyl, lower alkylsulfenyl, lower alkylsulfonyl, lower alkoxy, oxo, nitro, mercapto, amino optionally substituted by alkyl, carboxy, carbamoyl optionally substituted by alkyl, carboxamide optionally substituted by alkyl, aminosulfonyl optionally substituted by alkyl. Examples of aryl include, but are not limited to, phenyl, 2-naphthyl, 1-naphthyl, biphenyl, fluorenyl, indenyl, azulenyl and anthracenyl and the like.

As used herein, the term "heteroaryl" refers to a 5-7 membered unsaturated ring containing one or more heteroatoms selected from S, SO, $SO_2$, O or N, or to a fused bicyclic unsaturated ring comprising two such 5-7 membered unsaturated rings, said ring optionally substituted with lower alkyl, lower haloalkyl, lower alkylsufanyl, lower alkylsulfenyl, lower alkylsulfonyl, lower alkoxy, oxo, nitro, mercapto, amino optionally substituted by alkyl, carboxy, carbamoyl optionally substituted by alkyl, carboxamide optionally substituted by alkyl, aminosulfonyl optionally substituted by alkyl. Examples of heteroaryl used herein include, but are not limited to, furanyl, thiophenyl, pyrrolyl, isoquinolinyl, benzofuranyl, benzoimidazolyl, benzoxazolyl, benzoisoxazolyl, benzothiophenyl, benzothiazolyl, benzothiadiazolyl, benzotriazolyl, indolizinyl, indolyl, azaindolyl, isoindolyl, indazolyl, azaindazolyl, thiadiazolyl, isothiazolyl, pyridinyl, pyridazinyl, pyrazinyl, pyrimidinyl, purinyl, 4H-quinolizinyl, quinolinyl, isoquinolinyl, cinnolinyl, phthalzinyl, quinazolinyl, quinoxalinyl, imidazolyl, pyrazolyl, triazolyl, tetrazolyl, thiazolyl, isothiazolyl, oxazolyl, isoxazolyl, oxadiazolyl, indazolyl, naphthyridinyl, and pteridinyl and the like.

As used herein, acyl means the group —C(O)alkyl.

As used herein, aldehyde means the group —C(O)H.

As used herein, amine or amino means the group —$NH_2$.

As used herein, aminoalkyl means the group —NHR or $N(R)_2$, where R is $(C_{1-4})$alkyl.

As used herein, aminoacylamino means the group —NHCO-alkyl-NHR or —NHCO-alkyl-$N(R)_2$, where R is hydrogen or alkyl and NHR and $N(R)_2$ are each attached on any alkyl carbon atom.

As used herein, carbonyl or ketone means the group —C(O)—.

As used herein, carboxy or carboxyl means the group —C(O)OH.

As used herein, carboxamide, amido or carbamoyl means the group —C(O)$NH_2$.

As used herein, carbamoyl$(C_{1-4})$alkyl means the group —C(O)NHR or —C(O)$N(R)_2$, where R is $(C_{1-4})$alkyl as defined herein.

As used herein, ester means the group —C(O)OR, where R is alkyl, cycloalkyl, heterocyclyl, aryl, or heteroaryl as defined herein.

As used herein, halogen or halo means the group chloro, bromo, fluoro or iodo.

As used herein, haloalkyl means the group -alkyl(halo)$_{1-3}$ and includes monofluoromethyl, difluoromethyl, trifluoromethyl, trifluoroethyl and the like.

As used herein, haloalkoxy means the group -alkoxy (halo)$_{1-3}$ and includes monofluoromethoxy, difluoromethoxy, trifluoromethoxy, trifluoroethoxy and the like.

As used herein, mercapto means the group —SH.

As used herein, phosphine means the group —PH$_3$.

As used herein, phosphonato means the group —OP(O)OR, where R is hydrogen or alkyl.

As used herein, sulfanyl or thiol means the group —S—.

As used herein, sulfenyl or sulfinyl means the group —SO—.

As used herein, sulfonyl means the group —SO$_2$—.

As used herein, sulfo means the group —SO$_2$OH.

As used herein, aminosulfonyl means the group —SO$_2$NH$_2$.

As used herein, sulphamoyl, sulfamoyl or sulfonamide means the group —SO$_2$NHR or —SO$_2$N(R)$_2$, where R is hydrogen or alkyl, cycloalkyl, heterocyclyl, aryl, or heteroaryl as defined herein.

As used herein, thio(C$_{1-4}$)alkyl means the group —S—C$_{1-4}$)alkyl.

As used herein, thiocarbonyl means the group —C(S)R, where R is alkyl, cycloalkyl, heterocyclyl, aryl, or heteroaryl as defined herein.

As used herein, thioether means the group —SH$_2$.

As used herein, oxycarbamoyl means the group —OC(O)NHR, where R is hydrogen or alkyl, cycloalkyl, heterocyclyl, aryl, or heteroaryl as defined herein.

Some compounds described herein may contain one or more chiral centers. Therefore, the compounds of this invention may include pure enantiomers or enantiomerically enriched mixtures or racemates. Also within the scope of the invention are the individual isomers of the compounds represented by formula (I), (II) and (III) above or equilibrated mixtures.

The invention also relates to the compounds of formula (I), (II) and (III) in different crystalline forms, polymorphic forms and (an)hydrous forms. It is well known within the pharmaceutical industry that chemical compounds may be isolated in any of such forms by slightly changing the method of purification and/or isolation from the solvents used in the synthetic preparation of such compounds.

In one embodiment of this invention, there is provided a compound of formula (I):

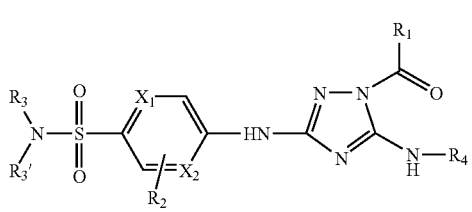

(I)

wherein:

$X_1$, $X_2$ are independently selected from CH and N, $R_1$ is a carbocyclic, heterocyclic or heteroaryl, wherein $R_1$ is optionally substituted with one or more substitutents independently selected from amido, phosphonato, phosphine, carboxyl, thiocarbonyl, sulfonyl, nitro, thiol, thioether, amine, cyano, N—(C$_{1-6}$-alkyl)amino, N,N—(C$_{1-6}$-alkyl)$_2$ amino, sulfonamide, ketone, aldehyde, ester, halogen, oxygen, haloalkyl, C$_{1-6}$-alkyl, C$_{2-6}$-alkenyl, C$_{2-6}$-alkynyl, hydroxyl, or C$_{1-6}$-alkoxyl, $R_2$ is hydrogen, hydroxy, nitro, amino, carboxy, carbamoyl, halo, cyano, trifluoromethyl, trifluoromethoxy, sulphamoyl, mercapto, C$_{1-6}$-alkyl, C$_{2-6}$-alkenyl, C$_{2-6}$-alkynyl, C$_{1-6}$-alkoxyl, N—(C$_{1-6}$-alkyl)amino, N,N—(C$_{1-6}$-alkyl)$_2$amino, or sulfonyl, $R_3$ and $R_4$ are independently selected from hydrogen, —CH$_2$OPO$_3$R$_5$R$_6$, —CH$_2$OCOR$_7$, —CH$_2$OCO$_2$R$_7$, —CH$_2$OCONHR$_7$, —COR$_7$, or —CONHR$_7$, wherein $R_3$ and $R_4$ are not simultaneously hydrogen, $R_3'$ is selected from the group consisting of hydrogen, heterocyclic or C$_{1-8}$alkyl, wherein C$_{1-8}$alkyl is optionally substituted with one or more of —CO$_2$H, —CO$_2$(C$_{1-6}$)alkyl, hydroxy, C$_{1-6}$alkoxy, amino, aminoacylamino, N—(C$_{1-6}$-alkyl)amino, N,N—(C$_{1-6}$alkyl)$_2$amino, heterocyclic or heteroaryl, $R_5$ and $R_6$ are selected from hydrogen, C$_{1-6}$alkyl, Na, K and NH$_4$ and are the same unless either $R_5$ or $R_6$ is absent, hydrogen or C$_{1-6}$alkyl, in which case the other is different, or alternatively, $R_5$ and $R_6$ together represent calcium, or magnesium, $R_7$ is heterocyclic or C$_{1-6}$alkyl, wherein C$_{1-6}$alkyl is optionally substituted with one or more of —CO$_2$H, —CO$_2$(C$_{1-6}$)alkyl, amino, amino-COR$_8$, carbamoyl, carbamoyl(C$_{1-6}$)alkyl, guanidino, mercapto, thio(C$_{1-6}$)alkyl, hydroxy, N—(C$_{1-6}$-alkyl)amino, N,N—(C$_{1-6}$-alkyl)$_2$amino, aryl optionally substituted on aryl with one or more of C$_{1-4}$alkyl, C$_{1-4}$alkoxy, hydroxy, halogen, amino, aminoalkyl, nitro or cyano, heterocyclic, —(OCH$_2$CH$_2$)$_n$OCH$_3$ where n is 0-400, —(OCH$_2$CH$_2$)$_n$OH where n is 0-400, or —(OCH$_2$CH$_2$)$_n$OCH$_2$CO$_2$H where n is 0-400, and $R_8$ is C$_{1-6}$alkyl optionally substituted with one or more of —CO$_2$H, —CO$_2$(C$_{1-6}$)alkyl, amino, aminoacylamino, carbamoyl, carbamoyl(C$_{1-6}$)alkyl, guanidino, mercapto, thio (C$_{1-6}$)alkyl, hydroxy, N—(C$_{1-6}$-alkyl)amino, N,N—(C$_{1-6}$-alkyl)$_2$amino, aryl optionally substituted on aryl with one or more of C$_{1-4}$alkyl, C$_{1-4}$alkoxy, hydroxy, halogen, amino, aminoalkyl, nitro or cyano, heterocyclic, —(OCH$_2$CH$_2$)$_n$OCH$_3$ where n is 0-400, —(OCH$_2$CH$_2$)$_n$OH where n is 0-400, or —(OCH$_2$CH$_2$)$_n$OCH$_2$CO$_2$H where n is 0-400.

In another embodiment of this invention, there is provided a compound of formula (II):

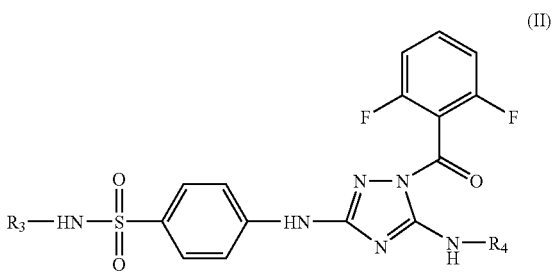

(II)

wherein:

$R_3$ and $R_4$ are independently selected from hydrogen, —CH$_2$OPO$_3$R$_5$R$_6$, —CH$_2$OCOR$_7$, —CH$_2$OCO$_2$R$_7$, —CH$_2$OCONHR$_7$, —COR$_7$, or —CONHR$_7$, wherein $R_3$ and $R_4$ are not simultaneously hydrogen, $R_5$ and $R_6$ are each selected from hydrogen, C$_{1-6}$alkyl, Na, K and NH$_4$ and are the same unless either $R_5$ or $R_6$ is absent, hydrogen or $C_{1-6}$alkyl, in which case the other is different, or alternatively, $R_5$ and $R_6$ together represent calcium, or magnesium, $R_7$ is heterocyclic or $C_{1-6}$alkyl, wherein $C_{1-6}$alkyl is optionally substituted with one or more of —$CO_2H$, —$CO_2(C_{1-6})$alkyl, amino, amino-$COR_8$, carbamoyl, carbamoyl($C_{1-6}$)alkyl, guanidino, mercapto, thio($C_{1-6}$)alkyl, hydroxy, N—($C_{1-6}$-alkyl)amino, N,N—($C_{1-6}$-alkyl)$_2$amino, aryl optionally substituted on aryl with one or more of $C_{1-4}$alkyl, $C_{1-4}$alkoxy, hydroxy, halogen, amino, aminoalkyl, nitro or cyano, heterocyclic, —(OCH$_2$CH$_2$)$_n$OCH$_3$ where n is 0-400, —(OCH$_2$CH$_2$)$_n$OH where n is 0-400, or —(OCH$_2$CH$_2$)$_n$OCH$_2$CO$_2$H where n is 0-400, and $R_8$ is $C_{1-6}$alkyl optionally substituted with one or more of —$CO_2H$, —$CO_2(C_{1-6})$alkyl, amino, aminoacylamino, carbamoyl, carbamoyl($C_{1-6}$)alkyl, guanidino, mercapto, thio($C_{1-6}$)alkyl, hydroxy, N—($C_{1-6}$-alkyl)amino, N,N—($C_{1-6}$-alkyl)$_2$amino, aryl optionally substituted on aryl with one or more of $C_{1-4}$alkyl, $C_{1-4}$alkoxy, hydroxy, halogen, amino, aminoalkyl, nitro or cyano, heterocyclic, —(OCH$_2$CH$_2$)$_n$OCH$_3$ where n is 0-400, —(OCH$_2$CH$_2$)$_n$OH where n is 0-400, or —(OCH$_2$CH$_2$)$_n$OCH$_2$CO$_2$H where n is 0-400.

In another embodiment of this invention, there is provided a compound of formula (III):

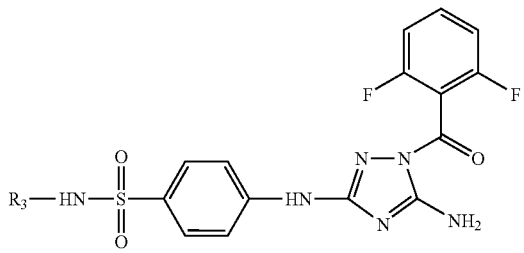

(III)

wherein:

$R_3$ is —$COR_7$, $R_7$ is heterocyclic or $C_{1-6}$alkyl, wherein $C_{1-6}$alkyl is optionally substituted with one or more of —$CO_2H$, —$CO_2(C_{1-6})$alkyl, amino, amino-$COR_8$, carbamoyl, carbamoyl($C_{1-6}$)alkyl, guanidino, mercapto, thio($C_{1-6}$)alkyl, hydroxy, N—($C_{1-6}$-alkyl)amino, N,N—($C_{1-6}$-alkyl)$_2$amino, aryl optionally substituted on aryl with one or more of $C_{1-4}$alkyl, $C_{1-4}$alkoxy, hydroxy, halogen, amino, aminoalkyl, nitro or cyano, heterocyclic, —(OCH$_2$CH$_2$)$_n$OCH$_3$ where n is 0-400, —(OCH$_2$CH$_2$)$_n$OH where n is 0-400, or —(OCH$_2$CH$_2$)$_n$OCH$_2$CO$_2$H where n is 0-400, and $R_8$ is $C_{1-6}$alkyl optionally substituted with one or more of —$CO_2H$, —$CO_2(C_{1-6})$alkyl, amino, aminoacylamino, carbamoyl, carbamoyl($C_{1-6}$)alkyl, guanidino, mercapto, thio($C_{1-6}$)alkyl, hydroxy, N—($C_{1-6}$-alkyl)amino, N,N—($C_{1-6}$-alkyl)$_2$amino, aryl optionally substituted on aryl with one or more of $C_{1-4}$alkyl, $C_{1-4}$alkoxy, hydroxy, halogen, amino, aminoalkyl, nitro or cyano, heterocyclic, —(OCH$_2$CH$_2$)$_n$OCH$_3$ where n is 0-400, —(OCH$_2$CH$_2$)$_n$OH where n is 0-400, or —(OCH$_2$CH$_2$)$_n$OCH$_2$CO$_2$H where n is 0-400.

Typically, pharmaceutically acceptable salts are non-toxic and could be formed by treating the compounds of the present invention with appropriate acids or bases by any suitable methods in the art. These acids include hydrochloric acid, hydrobromic acid, sulfuric acid, nitric acid, phosphoric acid, an amino acid such as aspartic acid or glutamic acid, aromatic acid such as benzoic acid or cinnamic acid, a sulfonic acid such as p-toluenesulfonic acid or ethanesulfonic acid, an α-OH acid such as citric acid and tartaric acid, a pyranosidyl acid such as glucuronic acid or galacturonic acid, acetic acid, maleic acid, succinic acid, mandelic acid, fumaric acid, malonic acid, pyruvic acid, oxalic acid, glycolic acid, salicylic acid. If the compounds of the present invention are acids, the pharmaceutically acceptable salt could be prepared by treating the free acid with an inorganic or organic base, including amino acids such as glycine and arginine, ammonia, amine (primary, second amine or tertiary), cyclic amines such as piperidine, pyrrolidine, piperazine and morpholine, NaOH, Ca(OH)$_2$, KOH, Mg(OH)$_2$, Fe(OH)$_3$, Cu(OH)$_2$, LiOH, Zn(OH)$_2$, and Al(OH)$_3$.

The present invention includes a pharmaceutical composition containing a compound of the formula (I), (II) or (III), or a pharmaceutically acceptable salt of a compound of the formula (I), (II) or (III); or a pharmaceutically active metabolite of a compound of the formula (I), (II) or (III), or a pharmaceutically acceptable salt of the metabolite, and the therapeutic use of the composition in treating a kinase mediated disease.

The present invention includes a method for treating or preventing a kinase mediated disease in a subject in need thereof comprising administering to the subject an effective amount of said compound.

The present invention includes a method for treating or preventing a cyclin dependent kinase mediated disease in a subject in need thereof comprising administering to the subject an effective amount of said compound.

The method further comprises administering to the subject an effective amount of a compound of formula (I), (II) or (III) or a pharmaceutically acceptable salt, active metabolite, salt of the metabolite or composition thereof in the form of a medicament.

As used herein, the term "effective amount" further means an amount in a range of from about 0.001 mg/kg to about 300 mg/kg of body weight per day. The term also includes compounds of the present invention having an IC$_{50}$ (50% inhibition concentration) of about 50 μM or less, about 25 μM or less, about 15 μM or less, about 10 μM or less, about 1 μM or less, about 0.5 μM or less, or about 0.1 μM or less.

The term "kinase mediated disease" as used herein, includes, and is not limited to syndromes, disorders or diseases associated with unregulated kinase activity and conditions that accompany such activity.

The term "unregulated kinase activity" and "inappropriate protein kinase activity" refers to 1) increased or unregulated kinase expression or signaling, 2) increased kinase expression leading to unregulated cell proliferation, 3) increased kinase signalling leading to unregulated cell proliferation, or 4) mutations leading to constitutive kinase activation. The existence of unregulated kinase activity may be determined by procedures well known in the art.

The term "unregulated cell proliferation" and "unregulated cellular proliferation activity" refers to cell proliferation of one or more subset of cells in a multicellular organism resulting in harm (such as discomfort or decreased life expectancy) to the multicellular organism.

Furthermore, the term "kinase mediated disease" in any of the foregoing methods contemplates that the compounds of the present invention are therapeutically useful for treating, preventing or ameliorating kinase mediated syndromes, disorders, diseases or conditions such as, without limitation, acute and chronic inflammation, osteoarthritis, rheumatoid arthritis, synovial pannus invasion in arthritis, multiple sclerosis, myasthenia gravis, diabetes mellitus, diabetic angiopathies or retinopathy, ocular diseases with retinal vessel proliferation, inflammatory bowel disease, Crohn's disease, ulcerative colitis, bone diseases, transplant or bone marrow transplant rejection, lupus, chronic pancreatitis, cachexia, septic shock, fibroproliferative and differentiative skin diseases or disorders (such as papilloma formation, psoriasis, dermatitis, eczema, seborrhea and the like), central nervous system diseases (such as Alzheimer's disease, Parkinson's disease, depression and the like), cancers (including solid tumors and leukemias such as glioma cancers, epidermoid cancers, head and neck cancers, lung cancers, breast cancers, colorectal cancers, prostate cancers, gastric cancers, esophageal cancers, papillocarcinomas or Kaposi's sarcoma and the like and associated pathologies such as unregulated cell proliferation, tumor growth or vascularization or metastatic cancer cell invasion and migration and the like or leukemias or lymphomas), occular diseases (such as macular degeneration, diseases of the cornea, glaucoma and the like), autoimmune disease, viral infections (such as cytomegalovirus), heart disease (such as hemangioma atheroma, atherosclerosis and the like), neointima formation or transplantation-induced vasculopathies (such as arterial restenosis and the like), lung or pulmonary diseases (such as allergic-asthma, lung fibrosis or complications resulting from chronic obstructive pulmonary disorder and the like) or acute and chronic nephropathies (including kidney or renal diseases such as acute, subacute or chronic forms of glomerulonephritis or membranoproliferative glomerulonephritis, glomerulosclerosis, congenital multicystic renal dysplasia, kidney fibrosis and the like).

The term "administering," with respect to the methods of the present invention, refers to a means for treating, ameliorating or preventing a disease, disorder or syndrome as described herein with a compound specifically disclosed or a compound or prodrug thereof, which would obviously be included within the scope of the invention albeit not specifically disclosed for certain of the instant compounds.

Such methods include administering an effective amount of one or more compounds of formula (I) or a composition or medicament thereof at different times during the course of a therapy or concurrently in a combination form. Such methods further include therapeutically administering an effective amount of one or more compounds of formula (I) with one or more therapeutic agents at different times during the course of a therapy or concurrently in a combination form.

The term "prodrug" refers to a metabolic precursor of a compound of formula (I) or pharmaceutically acceptable form thereof. In general, a prodrug is a functional derivative of a compound which may be inactive when administered to a subject but is readily convertible in vivo into an active metabolite compound.

The term "active metabolite" refers to a metabolic product of a compound that is pharmaceutically acceptable and effective. Conventional procedures for the selection and preparation of suitable prodrug derivatives are described, for example, in "Design of Prodrugs", ed. H. Bundgaard, Elsevier, 1985.

The term "subject" as used herein, refers to an animal, a mammal, a human or a patient each being the object of treatment, observation or experiment and at risk of (or susceptible to) developing a disease or disorder or having a disease or disorder related to unregulated CDK activity.

The term "composition" refers to a product containing a compound of the present invention (such as a product comprising the specified ingredients in the specified amounts, as well as any product which results, directly or indirectly, from such combinations of the specified ingredients in the specified amounts).

The term "medicament" refers to a product for use in treating or ameliorating a kinase mediated disorder or condition.

The term "pharmaceutically acceptable" refers to molecular entities and compositions that are of sufficient purity and quality for use in the formulation of a composition or medicament of the present invention and that, when appropriately administered to an animal or a human, do not produce an adverse, allergic or other untoward reaction. Since both human use (clinical and over-the-counter) and veterinary use are equally included within the scope of the present invention, a pharmaceutically acceptable formulation would include a composition or medicament for either human or veterinary use.

The term "combination therapy" refers to the use of one or more compounds of formula (I) or composition or medicament thereof in combination with one or more therapeutic agents for the treatment of a number of different kinase mediated disorders and advantageously may facilitate the use of a reduced effective dose of the compound of formula (I) and/or the therapeutic agent than would be recommended for the treatment of a particular unregulated cell proliferation disorder. Therefore, it is contemplated that the compounds of this invention can be used before, during or after treatment with a particular therapeutic agent.

The term "therapeutic agent" refers to chemotherapeutic agents used to treat a CDK mediated cancer or antiviral agents used to treat cytomegalovirus. Chemotherapeutic agents include and are not limited to anti-angiogenic agents, anti-tumor agents, cytotoxic agents, inhibitors of cell proliferation, radiation therapy and the like or mixtures thereof.

The terms "treating" or "preventing" refer, without limitation, to facilitating the eradication of, inhibiting the progression of or promoting stasis of a malignancy.

The term "radiation therapy" refers to a therapy that comprises exposing the subject in need thereof to radiation. The present invention includes a method for administering one or more compounds of formula (I) or composition or medicament thereof in combination with radiation therapy. Procedures for administering such therapy are known to those skilled in the art. The appropriate scheme of radiation therapy will be similar to those already employed in clinical therapies wherein the radiation therapy is used alone or in combination with other chemotherapeutic agents.

Pharmaceutical formulations may be displayed as unit dose forms containing a predetermined amount of active ingredient per unit dose. Such a unit dose may contain about 1 mg to about 700 mg of a compound of the present invention depending on the condition being treated, the route of administration, etc. Typically, a physician will determine the actual dosage which will be most suitable for an individual patient and it will vary with the age, weight and response of the particular patient.

Pharmaceutical formulations may be prepared by any of the methods well known in the pharmacy art and may be adapted for administration by any appropriate route, for example by the oral (including buccal or sublingual), topical (including buccal, sublingual or transdermal), vaginal, parental (including intravenous, subcutaneous, intramuscular or intradermal), rectal, or nasal route.

Formulations for oral administration may be presented as capsules or tablets; powders or granules; solutions or suspensions in aqueous or non-aqueous liquids; oil-in-water liquid emulsions or water-in-oil liquid emulsion, edible foams or whips.

Formulations for topical administration may be presented as ointments, creams, suspensions, lotions, powders, solutions, pastes, gels, sprays, aerosols or oils.

Formulations for transdermal administration may be presented as discrete patches intended to remain in intimate contact with the epidermis of the recipient for a prolonged period of time.

Formulations for rectal administration may be presented as suppositories or as enemas.

Formulations for nasal administration may be presented as a nasal spray or as nasal drops and include aqueous or oil solutions of the active ingredient or a coarse powder having a particle size in the range of about 20 to about 500 microns.

Formulations for inhalation may be presented as fine particle dusts or mists, which may be generated by means of various types of metered dose, pressurized aerosols, nebulizers or insufflators.

Formulations for vaginal administration may be presented as pessaries, tampons, creams, gels, pastes, forms or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The compounds of the present invention or their pharmaceutically acceptable salts can also be administered through liposome delivery systems, such as small unilamellar vesicles, large unilamellar vesicles and multilamellar vesicles. Liposomes could be formed from a variety of phospholipids, such as stearylamine, phosphatidylcholine, or cholesterol.

The compounds of the present invention or their pharmaceutically acceptable salts can also be delivered by using monoclonal antibodies as carriers. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polyactic acid, polepsilon caprolactone, polyhydroxy butyric acid, polyorthoesters, polyacetals, polydihydropyrans, polycyanoacrylates and cross-linked or amphipathis block copolymers of hydrogels.

In the cancer therapeutic field it is common to use a combination of different treatments to cure cancer patients. Therefore, the antiproliferative activity defined herein could be used as a sole therapy or may involve one or more other substances and/or treatments. Such combinational treatment may be achieved by the simultaneous, sequential or separate administration of the individual component. The other component(s) for these conjoint treatments in addition to the antiproliferation therapy defined above include surgery, radiotherapy or chemotherapy. Such chemotherapy may cover three main categories of therapeutic agent:

1. Cell cycle specific chemotherapeutic agents including, but not limited to, epipodophyllotoxins (e.g., etoposide and teniposide); diterpenoids (e.g., paclitaxel and docetaxel); vinca alkaloids (e.g., vincristine, vindesine, vinblastine, and vinorelbine); antimetabolites (e.g., cladrabine, cytarabine, allopurinol, fludurabine, methotrexate, mercaptopurine, thioguanine, 5-fluorouracin and fluorodeoxyuridine) and camptothecins (e.g., 9-amino camptothecin, topotecan and irinotecan).

2. Cytotoxic chemotherapeutic agents including, but not limited to, alkylating agents (e.g., hexamethylmelamine, busulfan, melphalan, chlorambucil, cyclophosphamide, mechlorethamine, carmustine, lomustine, dacarbazine, carboplatin, displatin and oxaliplatin); antitumor antibiotics (e.g., bleomycin, idarubicin, mitomycin-c, doxorubicin, daunomycin, epirubicin, dactinomycin and mithramycin);

3. Other anticancer agents including, but not limited to, testosterone 5α-dihydroreductase inhibitors (e.g., finasteride); anti-estrogens (e.g., tamoxifen, toremifent, raloxifene, droloxifene and iodoxyfene); progestrogens (e.g., megestrol acetate); aromatase inhibitors (e.g., anastrozole, letrazole, vorazole, and exemestane; antiandrogens (e.g., flutamide, nilutamide, bicalutamide, and cytorterone acetate); LHRH agonists and antagonists (e.g., goserelin acetate and luprolide); metalloproteinase inhibitors (e.g., marimastat); urokinase plasminogen activator receptor function inhibitors; cyclooxygenase type 2 inhibitors (e.g., celecoxib); angiogenesis inhibiting agents such as VEGFR and TIE-2 inhibitors; growth factor function inhibitors such as inhibitors of hepatocyte growth factor; erb-B2, erb-B4, epidermal growth factor receptor (e.g., Iressa and Tarceva), platelet derived growth factor receptor, vascular endothelial growth factor receptor and TIE-2; other tyrosine kinase inhibitors in addition to those described in the present invention; and other serine/threonine kinase inhibitors in addition to those described in the present invention.

The most commonly used drug moiety is selected from paclitaxel, camptothecin, etoposide, doxorubicin, bohemine, methotrexate and podophyllotoxin.

Representative compounds for use in the therapeutic methods and pharmaceutical compositions described herein include compounds selected from:

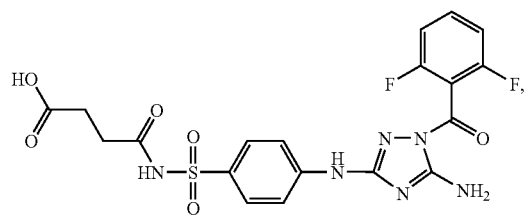

Cpd 1

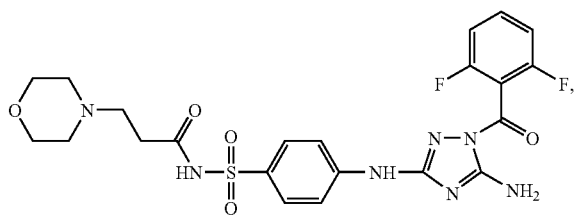

Cpd 7

-continued
Cpd 2
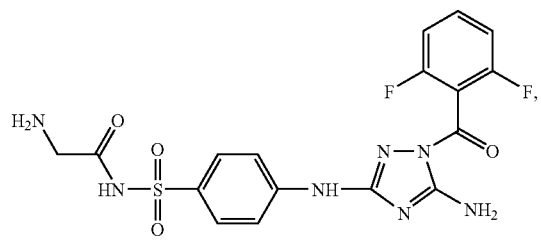
Cpd 13
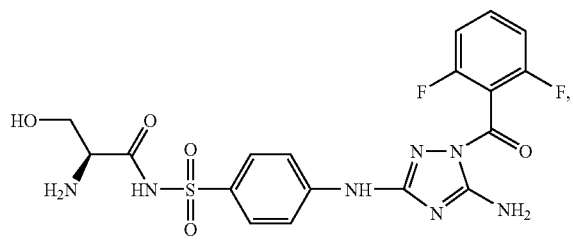
Cpd 12
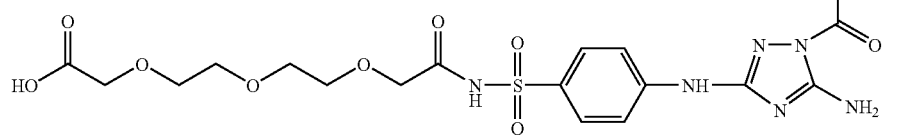
Cpd 14
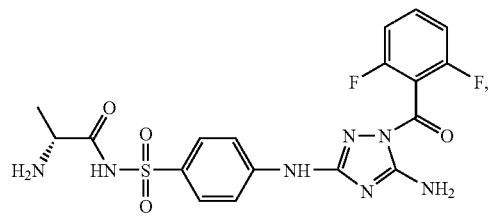
Cpd 15
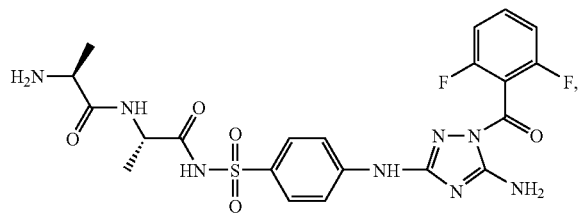
Cpd 4
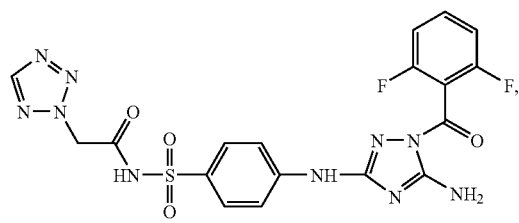
Cpd 3
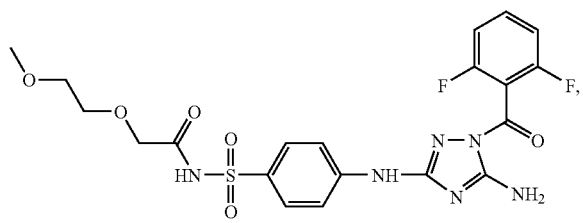
Cpd 5
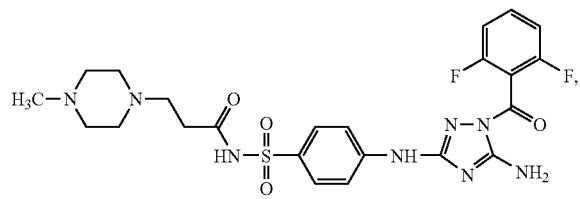
Cpd 6
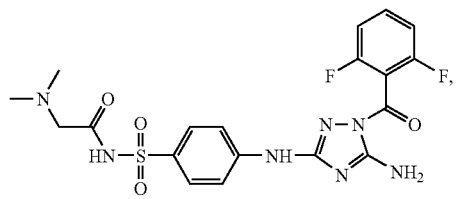
Cpd 11
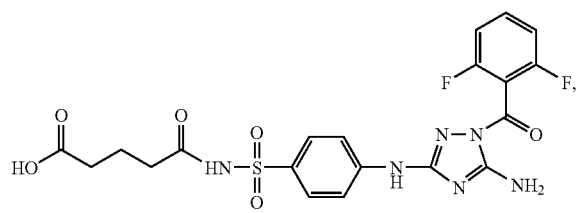
Cpd 18
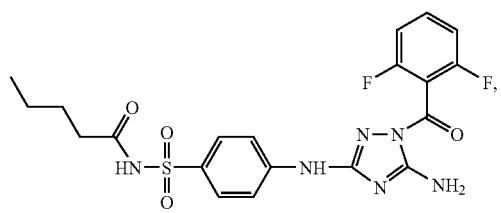

-continued

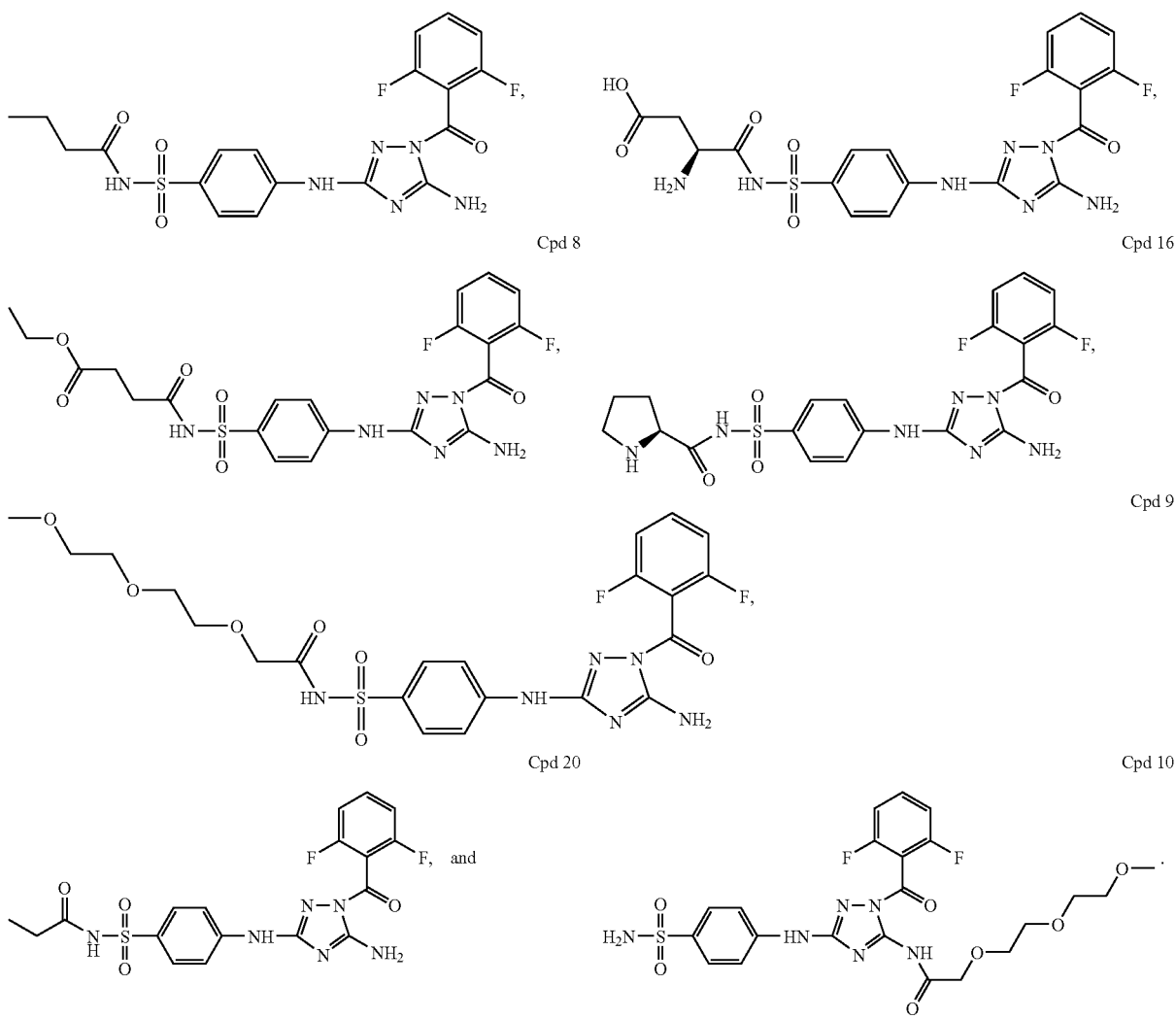

The compounds in accordance with this invention may be prepared using the reaction routes and synthesis schemes as described below, employing the techniques available in the art, using starting materials that are readily available.

Scheme A

In general, the process for preparing a compound of Formula (I) comprises the steps of a. reacting a compound of Formula A1 with a compound of Formula A2 to prepare a compound of Formula A3;

wherein the Formula A1 compound comprises a $PG_a$ suitable protecting group portion, a $R_a$ suitable linking group portion and a $Q_a$ suitable reaction group portion;

wherein the Formula A2 compound comprises a $Q_b$ suitable reaction group portion and a $PG_b$ suitable protecting group portion;

wherein the Formula A3 compound comprises a $PG_a$ suitable protecting group portion, a $R_a$ suitable linking group portion and a $Q_a$ suitable reaction group portion; wherein the $R_a$ linking group further incorporates certain portions of the $Q_a$ and $Q_b$ reaction groups as a product of the reaction;

b. transforming a compound of Formula A3 into a compound of Formula A4;

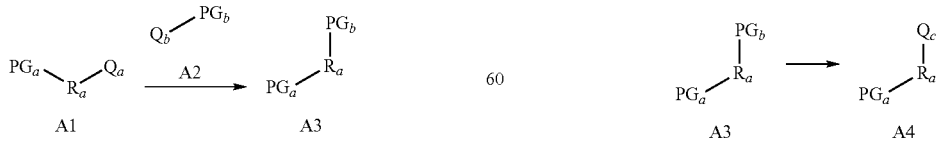

wherein the Formula A4 compound comprises a $PG_a$ suitable protecting group portion, a $R_a$ suitable linking group portion and a $Q_c$ suitable reaction group portion;

c. reacting a compound of Formula A5 with a compound of Formula A4 to prepare a compound of Formula A6;

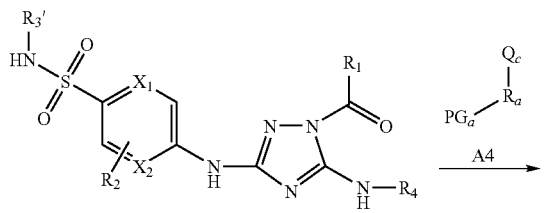

A5

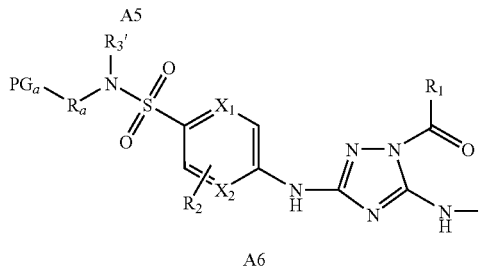

A6 d. transforming a compound of Formula A6 into a compound of Formula (I),

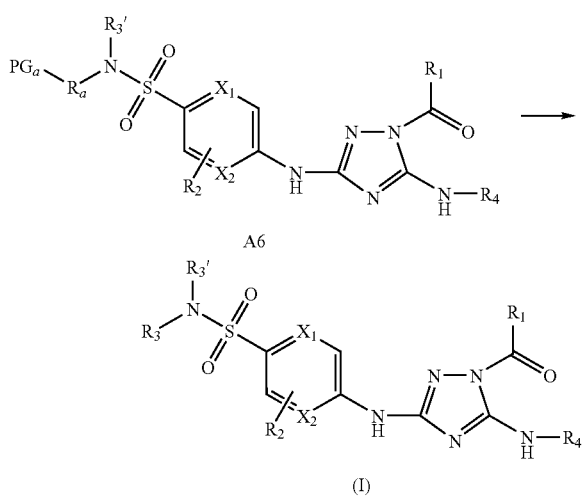

wherein the Formula (I) compound $R_3$ group incorporates certain portions of the $R_a$ linking group as a product of the reaction.

Scheme B

More specifically, the procedure for the generation of mixed anhydride compounds of Formula A3 includes:

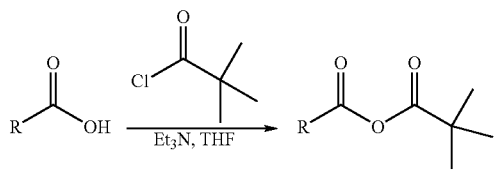

To a nitrogen purged flask was added THF, carboxylic acid and $Et_3N$. The mixture was cooled to 0° C. and pivaloyl chloride in THF was added dropwise. After addition the mixture was stirred at 0° C. for 1 hr, then filtered and the precipitate was washed with THF. The filtrate was concentrated and the product was used quickly without any purification.

Scheme C

In general, the process for preparing a compound of Formula (I) comprises the steps of More specifically, the procedure for the generation of mixed anhydride compounds of Formula A3 includes the steps:

More specifically, the procedure for the generation of prodrug compounds of Formula (I) includes the steps:

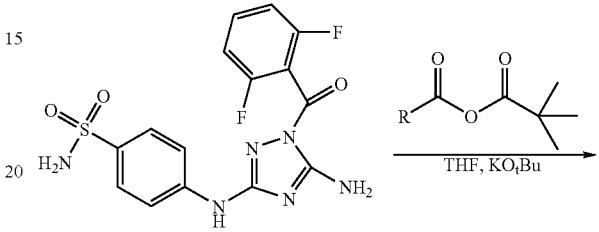

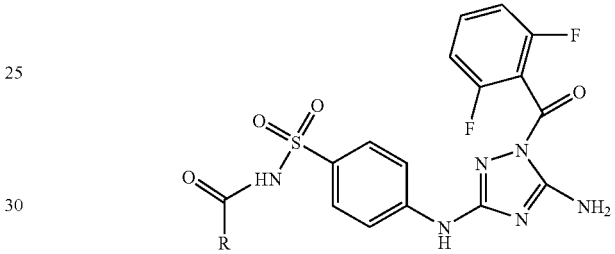

To a nitrogen purged flask was added 4-[5-amino-1-(2,6-difluorobenzoyl)-1H-[1,2,4]triazol-3-ylamino]-benzenesulfonamide (prepared as described in WO2002057240) and THF. The mixture was cooled to 0° C. and potassium tert-butoxide was added dropwise. After addition the mixture was stirred at 0° C. for 1 hr, then a mixed anhydride in THF was added dropwise. The stirring was continued for 30 min, then the mixture was warmed to room temperature (rt) and stirred overnight. After concentration, the residue was purified by flash chromatography.

Other known or commercially available cyclic or acyclic, symmetric or asymmetric anhydrides known to those skilled in the art may be used to prepare additional compounds which are representative of the scope of the present invention.

The following examples are set forth to aid in the understanding of the invention, and are not intended and should not be construed to limit in any way the invention set forth in the claims which follow thereafter.

Example 1

4-{4-[5-amino-1-(2,6-difluoro-benzoyl)-1H-[1,2,4] triazol-3-ylamino]-benzenesulfonylamino}-4-oxo-butyric acid (Cpd 1)

To a nitrogen purged flask was added 4-[5-amino-1-(2,6-difluorobenzoyl)-1H-[1,2,4]triazol-3-ylamino]-benzenesulfonamide Compound 1a (0.10 g, 0.25 mmol) and THF (10 mL). The mixture was cooled to 0° C. and potassium tert-butoxide (0.28 mL, 1.0 M solution in THF) was added dropwise. After addition the mixture was stirred at 0° C. for 1 hr, then succinic anhydride (28 mg in 5 mL THF, 0.28 mmol) was added dropwise. The stirring was continued for 30 min, then the mixture was warmed to rt and stirred overnight. A few drops of acetic acid was added, then the mixture was concentrated. The residue was purified by flash chromatography (silica gel, CH$_2$Cl$_2$:MeOH/8:2) to afford the desired product (39 mg, 31%) as a white solid. $^1$H NMR (300 MHz, CD$_3$OD) δ 7.70 (d, 2H), 7.63 (m, 1H), 7.42 (d, 2H), 7.15 (t, 2H), 2.41 (br s, 4H); MS (ESI) m/z: 493 (M+H)$^+$.

Example 2

N-(2-amino-acetyl)-4-[5-amino-1-(2,6-difluoro-benzoyl)-1H-[1,2,4]triazol-3-ylamino]-benzenesulfonamide (Cpd 2)

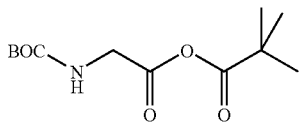

2a

Using the mixed anhydride formation procedure, 2.9 g (100%) of Compound 2a was formed from N-tert-butoxycarbonylglycine (2.0 g, 11.4 mmol) and pivaloyl chloride (1.55 mL in 5 mL THF, 12.4 mmol). $^1$H NMR (300 MHz, CDCl$_3$) δ 4.95 (br s, 1H), 4.01 (br s, 2H), 1.45 (s, 9H), 1.29 (s, 9H).

2b

Using the prodrug formation procedure, Compound 2b (250 mg, 15%) was generated from 4-[5-amino-1-(2,6-difluorobenzoyl)-1H-[1,2,4]triazol-3-ylamino]-benzenesulfonamide Compound 1a (1.5 g, 3.8 mmol), potassium tert-butoxide (4.2 mL, 1.0M solution in THF) and Compound 2a (1.2 g in 10 mL THF, 4.6 mmol). $^1$H NMR (300 MHz, DMSO) δ 9.58 (s, 2H), 7.92 (br s, 2H), 7.69 (p, 1H), 7.47 (d, 2H), 7.30 (m, 4H), 3.15 (d, 2H), 1.31 (s, 9H); MS (ESI) m/z: 550 (M+H)$^+$.

Compound 2b (0.20 g, 0.36 mmol) was suspended in CH$_2$Cl$_2$ (40 mL) and MsOH (1.0 mL) was added dropwise, then the mixture was stirred overnight. After being concentrated, EtOAc was added to precipitate the desired product, which was collected by filtration. 0.22 g (36%) of the salt was generated. $^1$H NMR (300 MHz, CD$_3$OD) δ 7.78 (d, 2H), 7.67 (p, 1H), 7.48 (d, 2H), 7.16 (t, 2H), 3.72 (s, 2H), 2.75 (s, 15H); MS (ESI) m/z: 450 (M+H)$^+$.

Example 3

4-[5-amino-1-(2,6-difluoro-benzoyl)-1H-[1,2,4]triazol-3-ylamino]-N-[2-(2-methoxy-ethoxy)-acetyl]-benzenesulfonamide (Cpd 3)

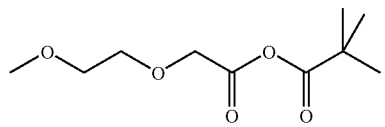

3a

Using the mixed anhydride formation procedure, 3.2 g (100%) of Compound 3a was generated from 2-(2-methoxyethoxy)acetic acid (2.0 g) and pivaloyl chloride (1.98 g). $^1$H NMR (300 MHz, CDCCl$_3$) δ 4.25 (s, 2H), 3.75 (m, 4H), 3.35 (s, 3H), 1.23 (s, 9H).

Using the prodrug formation procedure, 130 mg (11%) of Compound 3 was formed from 4-[5-amino-1-(2,6-difluorobenzoyl)-1H-[1,2,4]triazol-3-ylamino]-benzenesulfonamide Compound 1a (1.0 g) and Compound 3a (0.65 g). $^1$H NMR (300 MHz, CD$_3$OD) δ 7.78 (d, 2H), 7.68 (p, 1H), 7.50 (d, 2H), 7.16 (t, 2H), 3.96 (s, 3H), 3.59 (t, 2H), 3.52 (t, 2H), 3.35 (s, 3H); MS (ESI) m/z: 509 (M+H)$^+$.

Example 4

4-[5-amino-1-(2,6-difluoro-benzoyl)-1H-[1,2,4]triazol-3-ylamino]-N-(2-tetrazol-1-yl-acetyl)-benzenesulfonamide (Cpd 4)

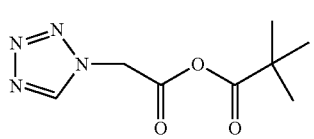

4a

Using the mixed anhydride formation procedure, 1.6 g (96%) of Compound 4a was generated from tetraazolylacetic acid (1.0 g) and pivaloyl chloride (1.0 g). $^1$H NMR (300 MHz, CDCCl$_3$) δ 8.90 (s, 1H), 5.45 (s, 2H), 1.21 (s, 9H).

Using the prodrug formation procedure, 120 mg (10%) of 4 was formed from 4-[5-amino-1-(2,6-difluorobenzoyl)-1H-[1,2,4]triazol-3-ylamino]-benzenesulfonamide Compound 1a (1.0 g) and Compound 4a (0.65 g). $^1$H NMR (300 MHz, D$_2$O) δ 9.05 (s, 1H), 7.65 (m, 3H), 7.25 (d, 2H), 7.12 (t, 2H), 5.15 (s, 2H), 3.96 (s, 3H); MS (ESI) m/z: 503 (M+H)$^+$.

Example 5

4-[5-amino-1-(2,6-difluoro-benzoyl)-1H-[1,2,4]triazol-3-ylamino]-N-[3-(4-methyl-piperazin-1-yl)-propionyl]-benzenesulfonamide (Cpd 5)

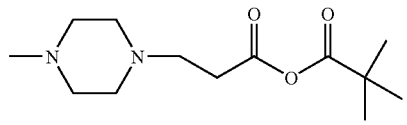

5a

Using the mixed anhydride formation procedure, 4.38 g (98%) of Compound 5a was generated from 3-N-methylpiperizinylpropionic acetic acid (3.0 g) and pivaloyl chloride (2.36 g). $^1$H NMR (300 MHz, CDCl$_3$) δ 2.75 (t, 2H), 2.65 (t, 2H), 2.60-2.40 (m, 4H), 2.25 (s, 3H), 1.21 (s, 9H).

Using the prodrug formation procedure, 190 mg (14%) of Compound 5 was formed from 4-[5-amino-1-(2,6-difluorobenzoyl)-1H-[1,2,4]triazol-3-ylamino]-benzenesulfonamide Compound 1a and Compound 5a (0.78 g). $^1$H NMR (300 MHz, DMSO) δ 9.80 (s, 2H), 8.00 (br s, 2H), 7.70 (p, 1H), 7.55 (d, 2H), 7.41 (d, 2H), 7.30 (t, 2H), 2.65 (t, 2H), 2.38 (br s, 4H), 2.20 (t, 2H), 2.15 (s, 3H); MS (ESI) m/z: 549 (M+H)$^+$.

Example 6

4-[5-amino-1-(2,6-difluoro-benzoyl)-1H-[1,2,4]triazol-3-ylamino]-N-(2-dimethylamino-acetyl)-benzenesulfonamide (Cpd 6)

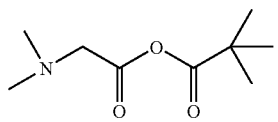

6a

Using the mixed anhydride formation procedure, 9.1 g (98%) of Compound 6a was generated from N,N-dimethylglycine (5.12 g) and pivaloyl chloride (6.73 g). $^1$H NMR (300 MHz, CDCCl$_3$) δ 3.30 (s, 2H), 2.35 (s, 6H), 1.21 (s, 9H).

Using the prodrug formation procedure, 180 mg (15%) of this prodrug was formed from 4-[5-amino-1-(2,6-difluorobenzoyl)-1H-[1,2,4]triazol-3-ylamino]-benzenesulfonamide Compound 1a and Compound 6a (0.57 g). $^1$H NMR (300 MHz, DMSO) δ 9.60 (s, 1H), 7.90 (br s, 2H), 7.70 (p, 1H), 7.55 (d, 2H), 7.35 (m, 4H), 3.48 (s, 2H), 2.65 (s, 6H); MS (ESI) m/z: 480 (M+H)$^+$.

Example 7

4-[5-amino-1-(2,6-difluoro-benzoyl)-1H-[1,2,4]triazol-3-ylamino]-N-(3-morpholin-4-yl-propionyl)-benzenesulfonamide (Cpd 7)

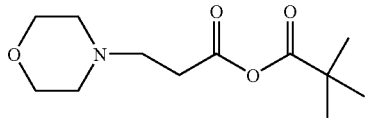

7a

Using the mixed anhydride formation procedure, 1.9 g (100%) of Compound 7a was generated from morpholinylpropionic acid (1.25 g) and pivaloyl chloride (1.05 g). $^1$H NMR (300 MHz, CDCl$_3$) δ 3.68 (m, 4H), 2.75 (t, 2H), 2.65 (t, 2H), 2.45 (m, 4H), 1.21 (s, 9H).

Using the prodrug formation procedure, 120 mg (9.6%) of Compound 7 was formed from 4-[5-amino-1-(2,6-difluorobenzoyl)-1H-[1,2,4]triazol-3-ylamino]-benzenesulfonamide Compound 1a (1.0 g) and Compound 7a (0.74 g). $^1$H NMR (300 MHz, DMSO) δ 9.95 (s, 1H), 7.90 (br s, 2H), 7.70 (p, 1H), 7.60 (d, 2H), 7.45 (d, 2H), 7.25 (t, 2H), 3.48 (s, 4H), 2.65 (m, 2H), 2.35 (m, 4H); MS (ESI) m/z: 536 (M+H)$^+$.

Example 8

4-{4-[5-amino-1-(2,6-difluoro-benzoyl)-1H-[1,2,4]triazol-3-ylamino]-benzenesulfonylamino}-4-oxobutyric acid ethyl ester (Cpd 8)

To a nitrogen purged flask was added 4-[5-amino-1-(2,6-difluorobenzoyl)-1H-[1,2,4]triazol-3-ylamino]-benzenesulfonamide Compound 1a (1.0 g, 2.5 mmol) and THF (100 mL). The mixture was cooled to 0° C. and potassium tert-butoxide (2.8 mL, 1.0 M solu in THF) was added dropwise. After addition the mixture was stirred at 0° C. for 1 hr, then ethyl 4-chloro-4-oxobutyrate (0.46 g in 10 mL THF, 2.8 mmol) was added dropwise. The stirring was continued for 30 min, then the mixture was warmed to rt and stirred overnight. After being concentrated, the residue was purified by flash chromatography (silica gel, CH$_2$Cl$_2$:MeOH/9:1) to afford the desired product (200 mg, 15%) as a white solid. $^1$H NMR (300 MHz, CD$_3$OD) δ 7.72 (d, 2H), 7.70 (m, 1H), 7.50 (d, 2H), 7.15 (t, 2H), 4.20 (q, 2H), 3.32 (s, 2H), 2.71 (s, 2H), 1.25 (t, 2H); MS (ESI) m/z: 523 (M+H)$^+$.

Example 9

4-[5-amino-1-(2,6-difluoro-benzoyl)-1H-[1,2,4]triazol-3-ylamino]-N-{2-[2-(2-methoxy-ethoxy)-ethoxy]-acetyl}-benzenesulfonamide (Cpd 9)

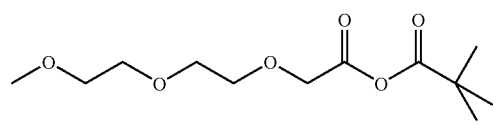

9a

Using the mixed anhydride formation procedure, 2.7 g (92%) of Compound 9a was generated from 2-2-methoxyethoxyethoxy acetic acid (2.00 g) and pivaloyl chloride (1.49 g). ¹H NMR (300 MHz, CDCl₃) δ 4.27 (s, 2H), 3.78 (t, J=7.0 Hz, 2H), 3.69 (t, J=6.9 Hz, 2H), 3.66 (t, J=7.0 Hz, 2H), 3.58 (t, J=7.0 Hz, 2H), 3.37 (s, 3H), 1.24 (s, 9H).

Using the prodrug formation procedure, 422 mg (15%) of Compound 9 was formed from 4-[5-amino-1-(2,6-difluorobenzoyl)-1H-[1,2,4]triazol-3-ylamino]-benzenesulfonamide Compound 1a (2.0 g) and Compound 9a (1.6 g). ¹H NMR (300 MHz, Acetone) δ 11.13 (br s, 1H), 9.20 (br s, 2H), 7.80 (p, J=6.9 Hz, 1H), 7.71 (d, J=7.0 Hz, 2H), 7.64 (d, J=7.0 Hz, 2H), 7.29 (t, J=7.0 Hz, 2H), 6.33 (br s, 2H), 3.86 (t, J=6.9 Hz, 2H), 3.75 (t, J=7.0 Hz, 2H), 3.60 (t, J=6.9 Hz, 2H), 3.48 (t, J=7.0 Hz), 3.21 (s, 3H); MS (ESI) m/z: 555 (M+H)⁺.

Example 10

N-[2-(2,6-difluoro-benzoyl)-5-(4-sulfamoyl-phenylamino)-2H-[1,2,4]triazol-3-yl]-2-[2-(2-methoxyethoxy)-ethoxy]-acetamide (Cpd 10)

Using the prodrug formation procedure, 394 mg (14%) of Compound 10 was formed from 4-[5-amino-1-(2,6-difluorobenzoyl)-1H-[1,2,4]triazol-3-ylamino]-benzenesulfonamide Compound 1a (2.0 g) and Compound 9a (1.6 g). ¹H NMR (300 MHz, Acetone) δ 10.23 (br s, 1H), 8.92 (br s, 1H), 7.83 (d, J=7.0 Hz, 2H), 7.75 (p, J=6.9 Hz, 1H), 7.63 (d, J=7.0 Hz, 2H), 7.50 (br s, 2H), 7.27 (t, J=7.0 Hz, 2H), 3.96 (s, 2H), 3.69 (t, J=6.9 Hz, 2H), 3.63 (br s, 6H), 3.29 (s, 3H).

Example 11

5-{4-[5-amino-1-(2,6-difluoro-benzoyl)-1H-[1,2,4]triazol-3-ylamino]-benzenesulfonylamino}-5-oxo-pentanoic acid (Cpd 11)

To a nitrogen purged flask was added 4-[5-amino-1-(2,6-difluorobenzoyl)-1H-[1,2,4]triazol-3-ylamino]-benzenesulfonamide Compound 1a (2.0 g, 5.1 mmol) and THF (200 mL). The mixture was cooled to 0° C. and potassium tert-butoxide (6.1 mL, 1.0 M solu in THF) was added dropwise. After addition the mixture was stirred at 0° C. for 1 hr, then glutaric anhydride (0.69 g in 10 mL THF, 6.0 mmol) was added dropwise. The stirring was continued for 30 min, then the mixture was warmed to rt and stirred overnight. A few drops of acetic acid was added, then the mixture was concentrated. The residue was purified by flash chromatography (silica gel, CH₂Cl₂:MeOH/8:2) to afford the desired product Compound 11 (670 mg, 26%) as a white solid. ¹H NMR (300 MHz, CD₃OD) δ 7.75 (d, J=7.0 Hz, 2H), 7.68 (m, 1H), 7.50 (d, J=6.9 Hz, 2H), 7.15 (t, J=6.9 Hz, 2H), 2.36 (t, J=6.8 Hz, 2H), 1.80 (t, J=6.8 Hz, 2H); MS (ESI) m/z: 493 (M+H)⁺.

Example 12

{2-[2-(2-{4-[5-amino-1-(2,6-difluoro-benzoyl)-1H-[1,2,4]triazol-3-ylamino]-benzenesulfonylamino}-2-oxo-ethoxy)-ethoxy]-ethoxy}-acetic acid.2TFA salt (Cpd 12)

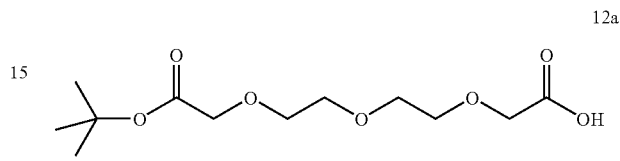

12a

To a flask was added 2-(2-carboxymethoxyethoxy)ethoxyacetic acid (17.0 g, 76.5 mmol), EDCI (22.0 g, 114.8 mmol), t-BuOH (5.7 g, 76.5 mmol), DMAP (0.9 g, 7.6 mmol) and DCM (300 mL). The mixture was stirred overnight and then concentrated. The residue was dissolved in H2O, then extracted with EtOAc. The organic layer was separated, dried with MgSO₄, then concentrated and the residue was purified by flash chromatography [silica gel, DCM:MeOH/7:3] to afford 17.2 g (81%) of the desired product 2-(2-tert-butoxycarbonylmethoxy)ethoxyethoxy acetic acid Compound 12a. ¹H NMR (300 MHz, CDCl₃) δ 4.00 (s, 4H), 3.75 (m, 8H), 1.46 (s, 9H).

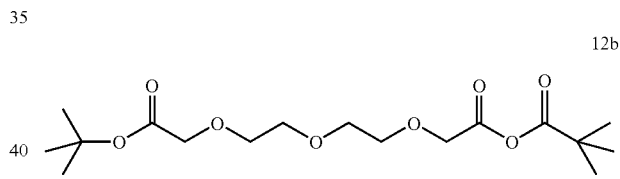

12b

Using the mixed anhydride formation procedure, 3.6 g (91%) of Compound 12b was generated from 2-(2-tert-butoxycarbonylmethoxy)ethoxyethoxy acetic acid Compound 12a (3.0 g) and pivaloyl chloride (1.4 g). ¹H NMR (300 MHz, CDCl₃) δ 4.30 (s, 2H), 3.94 (s, 2H), 3.75 (m, 2H), 3.70 (m, 6H), 1.46 (s, 9H), 1.22 (s, 9H).

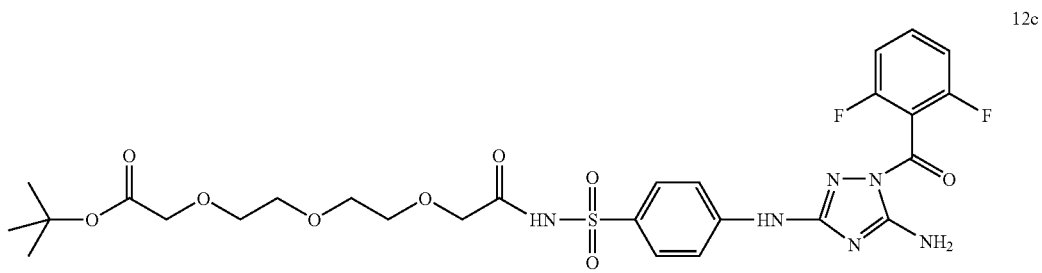

12c

Using the prodrug formation procedure, 790 mg (16%) of Compound 12c was formed from 4-[5-amino-1-(2,6-difluorobenzoyl)-1H-[1,2,4]triazol-3-ylamino]-benzenesulfonamide Compound 1a (3.0 g) and Compound 12b (3.3 g). $^1$H NMR (300 MHz, CDCl$_3$) δ 8.46 (br s, 1H), 7.78 (d, J=6.9 Hz, 1H), 7.55 (p, J=7.0 Hz, 1H), 7.36 (d, J=7.0 Hz, 2H), 7.05 (t, J=7.0 Hz, 2H), 5.90 (br s, 2H), 4.20 (s, 2H), 4.03 (s, 2H), 3.82 (m, 2H), 3.73 (m, 6H), 1.45 (s, 9H).

Compound 12c (50 mg) was dissolved in TFA (1 mL) and DCM (1 mL) and stirred for 2 hours. The solvent was removed in vacuo and the residue was washed with EtOAc to afford 56 mg (96%) of Compound 12. $^1$H NMR (300 MHz, CD3OD) δ 7.73 (m, 3H), 7.56 (d, J=7.0 Hz, 2H), 7.21 (t, J=6.9 Hz), 4.26 (s, 2H), 4.16 (s, 2H), 3.90-3.50 (m, 8H).

Example 13

4-[5-amino-1-(2,6-difluoro-benzoyl)-1H-[1,2,4]triazol-3-ylamino]-N—((S)-2-amino-3-hydroxy-propionyl)-benzenesulfonamide (Cpd 13)

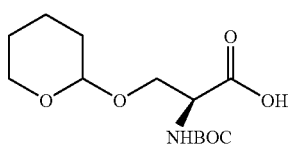

13a

To a flask was added N-Boc-L-serine (3.0 g, 14.6 mmol), PPTS (0.37 g, 1.47 mmol), dihydropyran (1.23 g, 14.6 mmol) and DCM (100 mL). The mixture was stirred at rt overnight, then concentrated. The residue was dissolved in EtOAc, washed with water. The organic layer was dried over MgSO$_4$, concentrated to afford 3.9 g (92%) of Compound 13a. $^1$H NMR (300 MHz, CDCl$_3$) 5.58 (m, 1H), 5.42 (diastereomer, m, 1H), 4.61 (m, 1H), 4.59 (diastereomer, m, 1H), 4.47 (m, 1H), 4.43 (diastereomer, m, 1H), 4.15 (m, 1H), 3.94 (m, 1H), 3.84 (diastereomer, m, 1H), 3.65 (diastereomer, m, 1H), 3.53 (m, 1H), 1.90-1.46 (m, 6H), 1.45 (s, 9H).

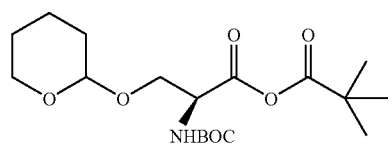

13b

Using the mixed anhydride formation procedure, 3.5 g (91%) of Compound 13b was generated from Compound 13a (3.0 g) and pivaloyl chloride (1.4 g). $^1$H NMR (300 MHz, CDCl$_3$) δ 5.55 (m 1H), 5.42 (diastereomer, m, 1H), 4.61 (m, 1H), 4.55 (diastereomer, m, 1H), 4.52 (m 1H), 4.19 (m, 1H), 3.93 (m, 1H), 3.84 (diastereomer, m, 1H), 3.65 (diastereomer, m, 1H), 3.50 (m, 1H), 1.90-1.50 (m, 6H), 1.45 (s, 9H), 1.23 (s, 9H).

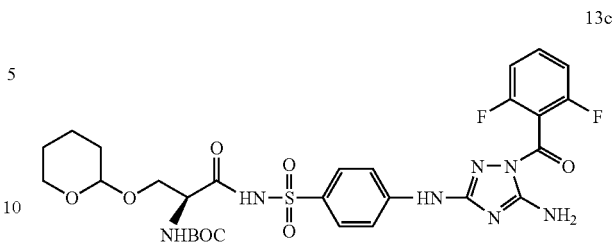

13c

Using the prodrug formation procedure, 410 mg (12%) of Compound 13c was formed from 4-[5-amino-1-(2,6-difluorobenzoyl)-1H-[1,2,4]triazol-3-ylamino]-benzenesulfonamide Compound 1a (2.0 g) and Compound 13b (2.3 g). $^1$H NMR (300 MHz, CDCl$_3$) δ 8.50 (s, 1H), 7.82 (d, J=7.0 Hz, 2H), 7.53 (m, 1H), 7.40 (d, J=6.9 Hz, 2H), 7.12 (s, 1H), 7.05 (t, J=7.0 Hz, 2H), 5.68 (m, 1H), 4.56 (m, 1H), 4.50 (m, 1H), 3.93 (diastereomer, m, 1H), 3.78 (m, 1H), 3.74 (m, 1H), 3.45 (m, 1H), 1.80-1.45 (m, 6H), 1.40 (s, 9H).

70 mg of Compound 13c was dissolved in MOH and conc. HCl was added. After stirring at room temperature overnight, the solvent was removed in vacuo and the residue was washed with EtOAc to afford 39 mg (62%) of the desired product Compound 13. $^1$H NMR (300 MHz, CD$_3$OD) δ 7.80 (d, J=7.0 Hz, 2H), 7.70 (p, J=6.9 Hz, 1H), 7.50 (d, J=7.0 Hz, 2H), 7.20 (t, J=7.0 Hz, 2H), 4.05-3.75 (m, 3H). MS (ESI) m/z: 482 (M+H)$^+$.

Example 14

4-[5-amino-1-(2,6-difluoro-benzoyl)-1H-[1,2,4]triazol-3-ylamino]-N—((R)-2-amino-propionyl)-benzenesulfonamide (Cpd 14)

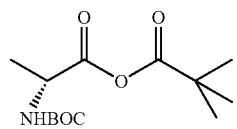

14a

Using the mixed anhydride formation procedure, 2.6 g (92%) of Compound 14a was generated from N-Boc-D-Ala (2.0 g) and pivaloyl chloride (1.4 g). $^1$H NMR (300 MHz, CDCl$_3$) δ 4.96 (br s, 1H), 4.40 (m, 1H), 1.46 (d, J=6.8 Hz), 1.45 (s, 9H), 1.25 (s, 9H).

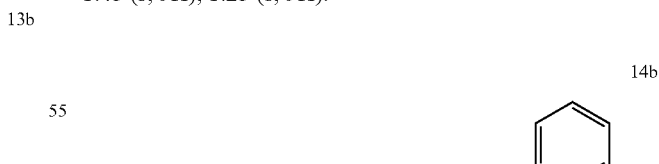

14b

Using the prodrug formation procedure, 470 mg (16%) of Compound 14b was formed from 4-[5-amino-1-(2,6-difluorobenzoyl)-1H-[1,2,4]triazol-3-ylamino]-benzenesulfonamide Compound 1a (2.0 g) and Compound 14a (1.7 g). $^1$H NMR (300 MHz, CD3OD) δ 7.78 (d, J=7.0 Hz, 1H), 7.68 (m, 1H), 7.52 (d, J=7.0 Hz, 2H), 7.12 (t, J=6.9 Hz, 2H), 4.01 (m, 1H), 1.32 (s, 9H), 1.21 (m, 3H).

Compound 14b (200 mg) was dissolved in mixed solvent of dichloromethane and TFA and stirred for 1 hr. The solvent was removed in vacuo and the residue was washed with EtOAc to afford 155 mg (46%) of Compound 14. $^1$H NMR (300 MHz, CD$_3$OD) δ 7.78 (d, J=7.0 Hz, 2H), 7.65 (p, J=6.9 Hz, 1H), 7.51 (d, J=7.0 Hz, 2H), 7.15 (t, J=7.0 Hz, 2H), 3.85 (q, J=7.1 Hz, 1H), 1.42 (d, J=7.1 Hz, 3H). MS (ESI) m/z: 466 (M+H)$^+$.

Example 15

(S)-2-amino-N—((S)-2-{4-[5-amino-1-(2,6-difluoro-benzoyl)-1H-[1,2,4]triazol-3-ylamino]-benzenesulfonylamino}-1-methyl-2-oxo-ethyl)-propionamide 3 TFA salt (Cpd 15)

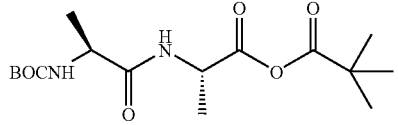

15a

Using the mixed anhydride formation procedure, 3.7 g (92%) of Compound 15a was generated from N-Boc-L-Ala-L-Ala (3.0 g) and pivaloyl chloride (1.5 g). $^1$H NMR (300 MHz, CDCl$_3$) δ 5.05 (br s, 1H), 4.60 (m, 1H), 4.20 (m, 1H), 1.50 (m, 15H), 1.22 (s, 9H).

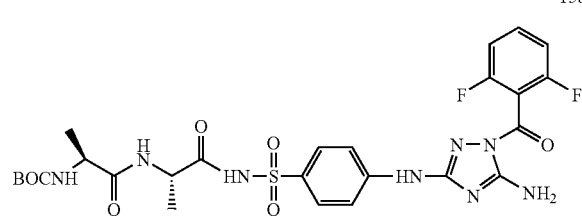

15b

Using the prodrug formation procedure, 580 mg (13%) of Compound 15b was formed from 4-[5-amino-1-(2,6-difluorobenzoyl)-1H-[1,2,4]triazol-3-ylamino]-benzenesulfonamide Compound 1a (3.0 g) and Compound 15a (3.3 g). $^1$H NMR (300 MHz, CD$_3$OD) δ $^1$H NMR (300 MHz, CD$_3$OD) δ 7.68 (d, J=7.0 Hz, 2H), 7.64 (p, J=6.9 Hz, 1H), 7.32 (d, J=7.0 Hz, 2H), 7.06 (t, J=7.0 Hz, 2H), 4.14 (m, 1H), 3.63 (m, 1H), 1.30 (m, 15H). MS (ESI) m/z: 636 (M+H)$^+$.

Compound 15b (200 mg) was dissolved in mixed solvent of dichloromethane and TFA and stirred for 1 hr. The solvent was removed in vacuo and the residue was washed with EtOAc to afford 116 mg (60%) of Compound 15. $^1$H NMR (300 MHz, CD3OD) δ 7.71 (d, J=7.0 Hz, 2H), 7.65 (p, J=6.9 Hz, 1H), 7.46 (d, J=7.0 Hz, 2H), 7.14 (t, J=7.0 Hz, 2H), 4.23 (m, 1H), 3.83 (m, 1H), 1.30 (m, 6H). MS (ESI) m/z: 537 (M+H)$^+$.

Example 16

4-[5-amino-1-(2,6-difluoro-benzoyl)-1H-[1,2,4]triazol-3-ylamino]-N—((S)-pyrrolidine-2-carbonyl)-benzenesulfonamide (Cpd 16)

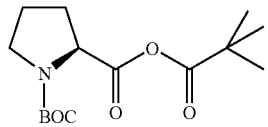

16a

Using the mixed anhydride formation procedure, 2.5 g (91%) of Compound 16a was generated from N-Boc-L-Pro (2.0 g) and pivaloyl chloride (1.1 g). $^1$H NMR (300 MHz, CDCl$_3$) δ 4.28 (m, 1H), 3.75 (m, 1H), 3.50 (m, 1H), 2.25 (m, 1H), 2.10 (m, 1H), 1.93 (m, 1H), 1.83 (m, 1H), 1.42 (s, 9H), 1.28 (s, 9H).

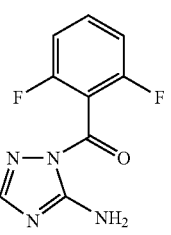

16b

Using the prodrug formation procedure, 420 mg (14%) of Compound 16b was formed from 4-[5-amino-1-(2,6-difluorobenzoyl)-1H-[1,2,4]triazol-3-ylamino]-benzenesulfonamide Compound 1a (2.0 g) and Compound 16a (1.8 g). $^1$H NMR (300 MHz, Acetone) δ 9.15 (s, 1H), 7.79 (p, J=6.8 Hz, 1H), 7.75 (d, J=6.9 Hz, 2H), 7.72 (d, J=7.0 Hz, 2H), 7.25 (t, J=7.0 Hz, 2H), 6.41 (br s, 2H), 4.52 (m, 1H), 3.55 (m, 2H), 2.40-1.90 (m, 4H), 1.40 (br s, 9H).

Compound 16b (100 mg) was dissolved in mixed solvent of dichloromethane and TFA and stirred for 1 hr. The solvent was removed in vacuo and the residue was washed with EtOAc, then the TFA salt was exchanged to HCl salt to afford 62 mg (62%) of Compound 16. $^1$H NMR (300 MHz, CD$_3$OD) δ 7.75 (p, J=6.9 Hz, 1H), 7.70 (d, J=7.0 Hz, 2H), 7.45 (d, J=7.0 Hz, 2H), 7.20 (d, J=6.9 Hz, 2H), 7.71 (m, 1H), 4.20 (m, 1H), 4.08 (m, 1H), 4.68 (m, 2H), 4.59 (m, 1H), 4.32 (m, 1H). MS (ESI) m/z: 492 (M+H)$^+$.

Example 17

(S)-3-amino-4-{4-[5-amino-1-(2,6-difluoro-benzoyl)-1H-[1,2,4]triazol-3-ylamino]-benzenesulfonylamino}-4-oxo-butyric acid (Cpd 17)

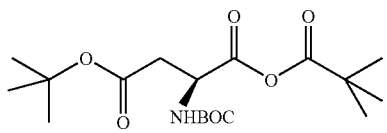

17a

Using the mixed anhydride formation procedure, 3.5 g (88%) of Compound 17a was generated from N-Boc-O-t-Bu-L-Asp (3.0 g) and pivaloyl chloride (1.4 g). $^1$H NMR (300 MHz, CDCl$_3$) δ 5.55 (m, 1H), 4.60 (m, 1H), 2.88 (m, 1H), 2.78 (m, 1H), 1.40 (s, 18H), 1.20 (s, 9H).

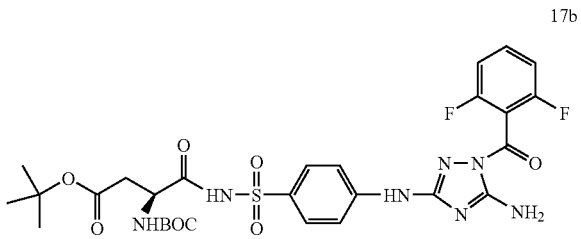

17b

Using the prodrug formation procedure, 500 mg (10%) of Compound 17b was formed from 4-[5-amino-1-(2,6-difluorobenzoyl)-1H-[1,2,4]triazol-3-ylamino]-benzenesulfonamide Compound 1a (3.0 g) and Compound 17a (3.4 g). $^1$H NMR (300 MHz, CD$_3$OD) δ 7.75 (d, J=6.8 Hz, 2H), 7.68 (p, J=6.8 Hz, 1H), 7.45 (d, J=6.9 Hz, 2H), 7.12 (d, J=7.0 Hz, 2H), 4.25 (m, 1H), 2.56 (m, 1H), 2.45 (m, 1H), 1.40 (s, 9H), 1.30 (s, 9H). MS (ESI) m/z: 664 (M–H)$^+$.

Compound 17b (200 mg) was dissolved in mixed solvent of dichloromethane and TFA and stirred for 1 hr. The solvent was removed in vacuo and the residue was washed with EtOAc, then the TFA salt was exchanged to HCl salt to afford 110 mg (59%) of Compound 17. $^1$H NMR (300 MHz, CD3OD) δ 7.80 (d, J=6.9 Hz, 2H), 7.78 (p, J=7.0 Hz, 1H), 7.50 (d, J=7.0 Hz, 2H), 7.15 (d, J=6.9 Hz, 2H), 3.65 (m, 1H), 3.90 (m, 2H), MS (ESI) m/z: 510 (M+H)$^+$.

Example 18

4-[5-amino-1-(2,6-difluoro-benzoyl)-1H-[1,2,4]triazol-3-ylamino]-N-pentanoyl-benzenesulfonamide (Cpd 18)

Compound 18 was prepared by the reaction of 4-[5-amino-1-(2,6-difluorobenzoyl)-1H-[1,2,4]triazol-3-ylamino]-benzenesulfonamide Compound 1a (100 mg, 0.254 mmol) with potassium-t-butoxide (0.305 mmol) for one hour at room temperature in anhydrous tetrahydrofuran (5 ml). Subsequent addition of valeryl chloride (0.305 mmol, 36.2 ul) and stirring for 16 hours at room temperature and purification by column chromatography in 5% methanol/dichloromethane gave Compound 18 in 17% yield. $^1$H NMR (400 MHz, DMSO) δ 11.75 (s, 1H), 9.99 (s, 1H), 8.02 (s, 2H), 7.71 (m, 1H), 7.65 (d, 2H), 7.49 (d, 2H), 7.35 (t, 2H), 2.14 (t, 2H), 1.36 (m, 2H), 1.14 (m, 2H), 0.77 (t, 3H); MS (ESI) m/z 479 (M+H$^+$), 501 (M+Na$^+$).

Example 19

4-[5-amino-1-(2,6-difluoro-benzoyl)-1H-[1,2,4]triazol-3-ylamino]-N-butyryl-benzenesulfonamide (Cpd 19)

Compound 19 was prepared by the reaction of 4-[5-amino-1-(2,6-difluorobenzoyl)-1H-[1,2,4]triazol-3-ylamino]-benzenesulfonamide Compound 1a with butyryl chloride, and potassium-t-butoxide in anhydrous tetrahydrofuran in a 14% yield. $^1$H NMR (400 MHz, DMSO) δ 11.75 (s, 1H), 9.99 (s, 1H), 8.02 (s, 2H), 7.71 (m, 1H), 7.65 (d, 2H), 7.49 (d, 2H), 7.35 (t, 2H), 2.12 (t, 2H), 1.40 (q, 2H), 0.73 (t, 3H); MS (ESI) m/z 464 (M+H$^+$), 487 (M+Na$^+$).

Example 20

4-[5-amino-1-(2,6-difluoro-benzoyl)-1H-[1,2,4]triazol-3-ylamino]-N-propionyl-benzenesulfonamide (Cpd 20)

Compound 20 was prepared by the reaction of 4-[5-amino-1-(2,6-difluorobenzoyl)-1H-[1,2,4]triazol-3-ylamino]-benzenesulfonamide Compound 1a with acetic anhydride, and potassium t-butoxide in anhydrous tetrahydrofuran in a 22% yield. $^1$H NMR (400 MHz, DMSO) δ 11.80 (s, 1H), 9.99 (s, 1H), 8.01 (s, 2H), 7.71 (m, 1H), 7.65 (d, 2H), 7.49 (d, 2H), 7.35 (t, 2H), 1.87 (s, 3H); MS (ESI) m/z 437 (M+H$^+$), 459 (M+Na$^+$).

Biochemical and Biological Evaluation

Selected compounds from the above example were investigated for their kinase activity. A panel of protein kinases, including CDK1, VEGFR and HER2 were used. The individual assays are described as follows:

CDK1 Screening Assay

A kinase reaction mixture was prepared containing 50 mM Tris-HCl pH=8, 10 mM MgCl$_2$, 0.1 mM Na$_3$PO$_4$, 1 mM DTT, 10 μM ATP, 0.025 μM biotinylated histone-H1 peptide substrate and 0.2 μCuries per well $^{33}$P-γ-ATP (2000-3000 Ci/mmol). 70 μL of the kinase reaction mixture was dispensed into each well of a streptavidin coated FlashPlate™ (Cat. # SMP103, NEN, Boston, Mass.). Then 1 μL of test compound stock in 100% DMSO was added to the wells resulting in a final concentration of 1% DMSO in the reaction with a 100 μl final reaction volume.

Next, CDK1:Cyclin-B protein was diluted in 50 mM Tris-HCl pH=8.0, 0.1% BSA at a concentration of 1 ng per μL and 30 μL (30 ng enzyme per test well) was added to each well to initiate the reaction. The reaction was incubated for one hour at 30° C. At the end of the 1 h incubation, the reaction was terminated by aspirating the mixture from the plate and washing the wells twice with PBS containing 100 mM EDTA. The histone-H1 biotinylated peptide substrate became immobilized on the Flashplate™ and the incorporation of $^{33}$P-γ-ATP was measured by reading the plate on a scintillation counter. Inhibition of the enzymatic activity of CDK1 was measured by observing a reduced amount of $^{33}$P-γ-ATP incorporated into the immobilized peptide.

CDK2 Screening Assay

A kinase reaction mixture was prepared containing 50 mM Tris-HCl pH=8, 10 mM MgCl$_2$, 0.1 mM Na$_3$PO$_4$, 1 mM DTT, 10 μM ATP, 0.025 μM biotinylated histone-H1 peptide substrate and 0.2 μCuries per well $^{33P}$-γ-ATP (2000-3000 Ci/mmol). 70 μL of the kinase reaction mixture was dispensed into the well of a streptavidin coated FlashPlate™ (Cat. # SMP103, NEN, Boston, Mass.). Then 1 μL of test compound stock in 100% DMSO was added to the wells resulting in a final concentration of 1% DMSO in the reaction with a 100 μl final reaction volume. Next, CDK2:Cyclin-E protein was diluted in 50 mM Tris-HCl pH=8.0, 0.1% BSA at a concentration of 1 ng per μL and 30 μL (30 ng enzyme per test well) was added to each well to initiate the reaction. The reaction was incubated for one hour at 30° C. At the end of the 1 h incubation, the reaction was terminated by aspirating the mixture from the plate and washing the wells twice with PBS containing 100 mM EDTA. The histone-H1 biotinylated peptide substrate became immobilized on the Flashplate™ and the incorporation of $^{33}$P-γ-ATP was measured by reading the plate on a scintillation counter. Inhibition of the enzymatic activity of CDK2 was measured by observing a reduced amount of $^{33}$P-γ-ATP incorporated into the immobilized peptide.

VEGF-R2 Kinase Screening Assay

A kinase reaction mixture was prepared containing 50 mM Tris-HCl pH=8, 10 mM MgCl$_2$, 0.1 mM Na$_3$PO$_4$, 1 mM DTT, 10 μM ATP, 0.025 μM biotinylated peptide substrate and 0.8 μCuries per well $^{33}$P-γ-ATP (2000-3000 Ci/mmol). 70 μL of the kinase reaction mixture was dispensed into each well of a streptavidin coated FlashPlate™ (Cat. # SMP103, NEN, Boston, Mass.). Then 1 μL of test compound stock in 100% DMSO was added to the wells resulting in a final concentration of 1% DMSO in the reaction with a 100 μL final reaction volume. Next, soluble rat tyrosine kinase containing an N-terminal 6×HIS tag was diluted in 50 mM Tris-HCl pH=8.0, 0.1% BSA at a concentration of 5 ng per μL and 30 μL (150 ng enzyme per test well) was added to each well to initiate the reaction. The reaction was incubated for one hour at 30° C. At the end of the 1 h incubation, the reaction was terminated by aspirating the reaction mixture from the plate and washing the wells twice with PBS containing 100 mM EDTA. The PLC1 biotinylated peptide substrate became immobilized on the Flashplate™ and the incorporation of $^{33}$P-γ-ATP was measured by reading the plate on a scintillation counter. Inhibition of the enzymatic activity of the VEGF-R2 kinase was measured by observing a reduced amount of $^{33}$P-γ-ATP incorporated into the immobilized peptide.

HER2 Kinase Screening Assay

The HER2 kinase assay was carried out as described above for the VEGF-R kinase assay except that the enzyme was replaced with a human epidermal growth factor receptor-2 (HER2) construct contains a polyhistidine tag at the N-terminus followed by 24 additional amino acids and begins at amino acid 676 (Accession #M11730) followed by the remainder of the HER2 cytoplasmic domain.

Definition and Source of Kinase Enzymes

VEGF-R (vascular endothelial growth factor receptor-2) is a fusion protein containing a polyhistidine tag at the N-terminus followed by amino acids 786-1343 of the rat VEGF-R2 kinase domain (GenBank Accession #U93306). CDK1 (cyclin dependent kinase 1) was isolated from insect cells expressing both the human CDK1 catalytic subunit and its positive regulatory subunit cyclin B (New England Biolabs, Beverly, Mass., Cat. # 6020). CDK2 in complex with cyclin A is commercially available (Upstate Biotech, Lake Placid, N.Y.). The HER2 (human epidermal growth factor receptor-2) construct contains a polyhistidine tag at the N-terminus followed by 24 additional amino acids and begins at amino acid 676 followed by the remainder of the HER2 cytoplasmic domain.

| Peptide Substrates | |
|---|---|
| VEGF-R and HER2 | (Biotin) KHKKLAEGSAYEEV-Amide |
| CDK1 and CDK2 | (Biotin) KTPKKAKKPKTPKKAKKL-Amide |

Results of assays performed on compounds described above are provided below in Table I. IC$_{50}$s listed as >10 or >100 means less than 50% inhibition was observed at the highest concentration tested.

TABLE I

Inhibition of kinase activity (IC$_{50}$)

| Compound | IC$_{50}$ (μM) CDK1 | IC$_{50}$ (μM) CDK2 | IC$_{50}$ (μM) VEGFR | IC$_{50}$ (μM) HER2 |
|---|---|---|---|---|
| 1 | 0.49 | 0.07 | 1.66 | 10 |
| 2 | 1.07 | 0.12 | 1.97 | 10 |
| 3 | 1.66 | 0.25 | 2.56 | 10 |
| 4 | 5.39 | 0.43 | 2.34 | 10 |
| 5 | 1.34 | 0.27 | 1.88 | 10 |
| 6 | 2.13 | 0.32 | 1.22 | 10 |
| 7 | 1.55 | 0.12 | 1.65 | >100 |
| 8 | 0.47 | 0.06 | 0.47 | 1.23 |
| 9 | 4.69 | 0.44 | 100 | >100 |
| 10 | 2.55 | 0.30 | 1.76 | >100 |
| 11 | 12.37 | 1.53 | 2.77 | >100 |
| 12 | 0.76 | 0.08 | 16.78 | >100 |
| 13 | 1.41 | 0.14 | 1.54 | 10 |
| 14 | 0.74 | 0.06 | 0.89 | 10 |
| 15 | 1.36 | 0.10 | 2.03 | 10 |
| 16 | 0.23 | 0.03 | 7.31 | 50 |
| 17 | 0.98 | 0.09 | 1.56 | 20 |
| 18 | 1.93 | 0.47 | 1.54 | 5 |
| 19 | 0.28 | 0.05 | 0.77 | 5 |
| 20 | 1.82 | 0.28 | 1 | 10 |

Assay to Measure Inhibition of Cell Proliferation

The ability of a test compound to inhibit the proliferation of cell growth was determined by measuring incorporation of $^{14}$C-labelled thymidine into newly synthesized DNA within the cells. This method was used on cell lines derived from carcinomas originating from several tissues such as HeLa cervical adenocarcinoma (American Type Culture Collection (ATCC), Virginia, Cat. #CCL-2), A375 malignant melanoma (ATCC CRL-1619), and HCT-116 colon carcinoma (CCL-247). In this way the effect of a compound on cell growth of cells with many different phenotypes can be determined. Cells were trypsinized and counted and 3000-8000 cells were added to each well of a 96-well CytoStar tissue culture treated scintillating microplate (Amersham #RPNQ0160) in complete medium in a volume of 100 μl. Cells were incubated for 24 hours in complete medium at 37° C. in an atmosphere containing 5% CO$_2$.

Next, 1 μl of test compound in 100% DMSO was added to the wells of the plate. DMSO only was added to control wells. Cells were incubated for 24 more hours in complete medium at 37° C. in an atmosphere containing 5% CO$_2$. Methyl $^{14}$C-thymidine 56 mCi/mmol (NEN #NEC568 or Amersham #CFA532) was diluted in complete medium and 0.2 uCi/well was added to each well of the CytoStar plate in a volume of 20 ul. The plate was incubated for 24 hours at 37° C. plus 5% CO$_2$ in drug plus $^{14}$C-thymidine. The contents of the plate were discarded into a $^{14}C$ radioactive waste container by inverting the plate and the plate was washed twice with 200 µl PBS.

200 µl of PBS was added to each well. The top of the plate was sealed with a transparent plate sealer and a white plate backing sealer (Packard #6005199) was applied to the bottom of the plate. The degree of methyl $^{14}C$-thymidine incorporation was quantified on a Packard Top Count.

Antiproliferative effects of the compounds described above are provided below in table II. $IC_{50}s$ listed as >10 or >100 means less than 50% inhibition was observed at the highest concentration tested.

TABLE II

Inhibition of cancer cell proliferation ($IC_{50}$)

| Compound | $IC_{50}$ (µM) HeLa | $IC_{50}$ (µM) HCT116 | $IC_{50}$ (µM) A375 |
|---|---|---|---|
| 1 | 31.9 | >100 | 20.3 |
| 2 | 14.86 | 36.95 | 9.45 |
| 3 | >10 | >10 | >100 |
| 4 | >100 | >100 | >100 |
| 5 | >100 | >10 | >100 |
| 6 | >10 | >10 | >100 |
| 7 | 20.91 | 50.84 | >100 |
| 8 | 60.16 | 40.14 | >10 |
| 9 | >10 | >100 | >10 |
| 10 | >100 | >100 | >100 |
| 11 | >100 | >100 | >100 |
| 12 | 30.8 | >10 | >10 |
| 13 | 4.02 | 71.2 | >10 |
| 14 | 1.96 | 38.5 | 71.06 |
| 15 | 1.04 | 20.79 | 12.08 |
| 16 | 10.23 | 3.94 | 26.78 |
| 17 | 58.3 | 28.35 | >100 |
| 18 | 81.2 | >100 | >100 |
| 19 | 6.89 | 11.57 | 24.11 |
| 20 | 58.84 | >10 | >10 |

Standard Rat Pharmacokinetics (PK)

The conversion of prodrug to active form was evaluated using a standard rat PK protocol. The following procedure may be followed.

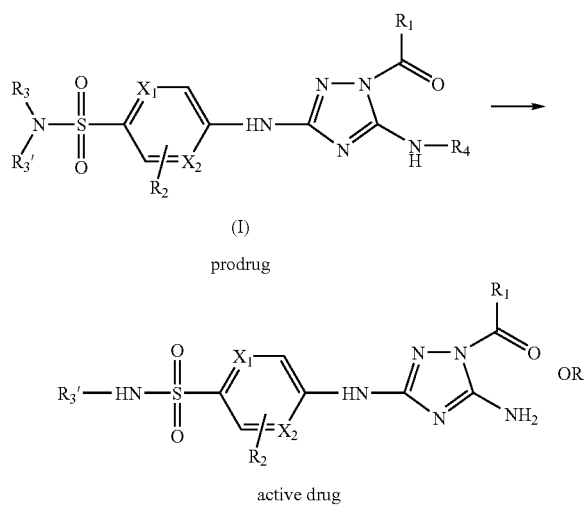

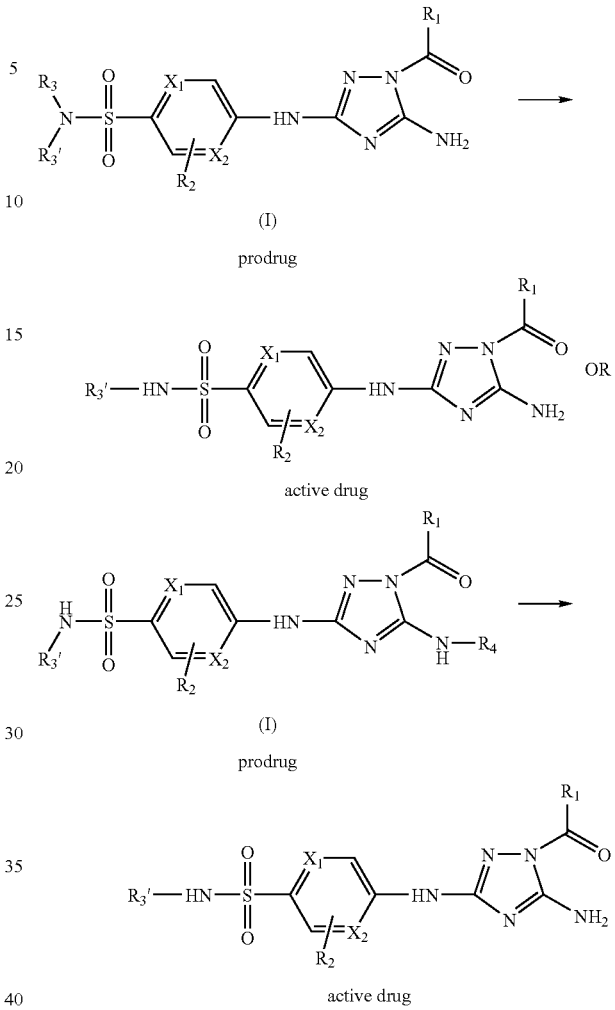

Rats were dosed intravenously (IV) at the level of 1.5-3 mg/kg and by oral gavage (PO) at the level of 10-30 mg/kg with prodrug candidate. For each study, four rats were used for IV dosing and four rats were used for PO dosing. Prodrug was typically formulated for IV dosing as a solution in 10% W/V solutol in 5% dextrose in sterile water vehicle (D5W). Prodrug was typically formulated for oral dosing as a uniform suspension in 0.5% methylcellulose vehicle. Blood samples (0.5 mL) were collected into heparinized tubes post dose via orbital sinus puncture. For IV dosing, blood samples were collected at 5, 15 and 30 mins, 1, 2, 4, 6, 8, and 24 hrs after the dosing. For PO dosing, blood samples were collected at 30 mins, 1, 2, 4, 6, 8 and 24 hrs. Blood samples were centrifuged for cell removal, and precisely 200 µL of plasma supernatant was then transferred to a clean vial, placed on dry ice, and subsequently stored in a −70° C. freezer prior to analysis. Results were calculated by WinNonlin Pro version 3.1. Plasma levels were determined and the oral and intravenous area under the concentration vs. time curve (AUC) were compared to determine the % bioavailability (% F) by the following formula: Dose(IV)*AUC(oral)/Dose (oral)*AUC(IV). The results of standard rat PK study for these prodrugs are shown in Table III.

TABLE III

Standard Rat PK

| Cpd | Dose (mg/kg) IV/PO | Prodrug $C_{max}$ (μM) IV | Drug $C_{max}$ (μM) IV | Prodrug $C_{max}$ (μM) PO | Drug $C_{max}$ (μM) PO | % F |
|---|---|---|---|---|---|---|
| 1 | 3/30 | 47 | 18 | 0.36 | 0.12 | 1 |
| 2 | 1.5/15 | 11.84 | 3.67 | 0 | 0.39 | 0 |
| 3 | 3/30 | 42.92 | 7.61 | 0.32 | 0.23 | 2 |
| 4 | 3/30 | 23.47 | 0 | 0 | 0 | 0 |
| 5 | 1.7/17 | 23.24 | 0.93 | 0 | 0 | 0 |
| 6 | 3/30 | 25.2 | 0.50 | 0 | 0 | 0 |
| 7 | 3/30 | 20.5 | 1.44 | 0 | 0 | 0 |
| 8 | 3/30 | 72.23 | 29.07 | 0.19 | 0.88 | 0.17 |
| 9 | 2/10 | 0 | 0.161 | 0 | 0.169 | 0 |
| 10 | 2/10 | 67.26 | 2.41 | 0 | 0.19 | 0 |
| 11 | 2/10 | 81.79 | 1.12 | 0.346 | 0 | 0 |
| 12 | 2/10 | 0 | 1.0 | 0.04 | 0 | 0 |
| 13 | 2/10 | 8.15 | 0.63 | 0 | 0 | 0 |
| 14 | 2/10 | 11.0 | 0.18 | 0.08 | 0.03 | 1 |
| 15 | 2/10 | 31.84 | 1.08 | 0.167 | 0.42 | 0 |
| 16 | 2/10 | 1.8 | 0.6 | 0 | 0 | 0 |
| 17 | 2/10 | 18.3 | 0.14 | 0.10 | 0.06 | 0 |
| 18 | 3/30 | 134.38 | 0.52 | 0.41 | 0 | 0.40 |
| 19 | 3/30 | 127.15 | 0 | 0.27 | 0 | 0.41 |
| 20 | 3/30 | 33.5 | 1.8 | 0.02 | 0.03 | 0.34 |

In Vivo Models—Inhibition of Tumor Growth

The in vivo effect of a compound on the growth of human tumor cells can be evaluated by implanting human tumor cells into the hindflank of athymic mice and administering test compound to the mice. Human tumor cells originating from a variety of different tumor types, such as A375 human melanoma cells, are implanted subcutaneously into the hindflank of male athymic mice (Charles River) and allowed to establish a sizeable tumor for 6-10 days as determined by caliper measurements. Test compound is then administered by injecting the compound formulated in an appropriate vehicle intraperitoneally into the mice once a day for 30 days. The test compound can also be administered by other routes such as orally, subcutaneously or by intravenous infusion. The size of the tumor in this study is measured every four days and the degree of inhibition is determined by comparing drug-treated animals to animals that are injected with vehicle only.

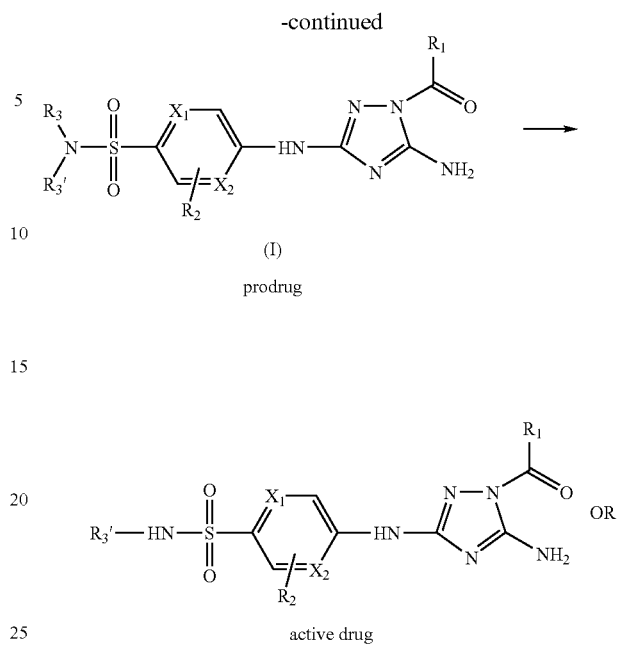

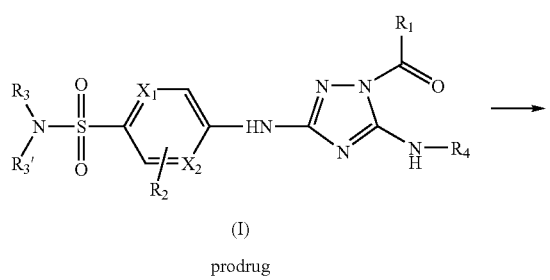

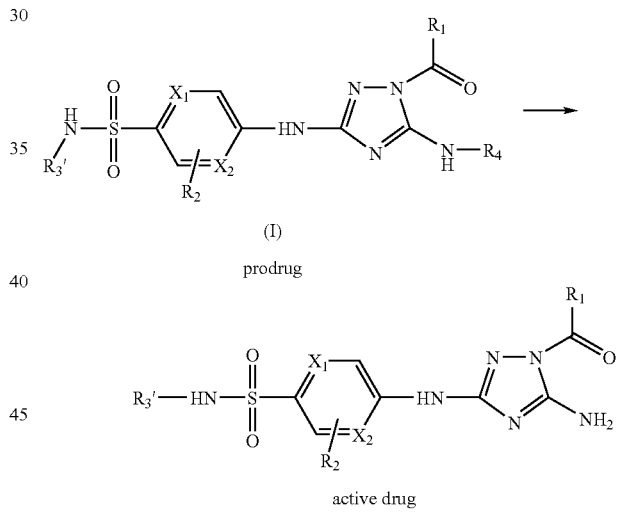

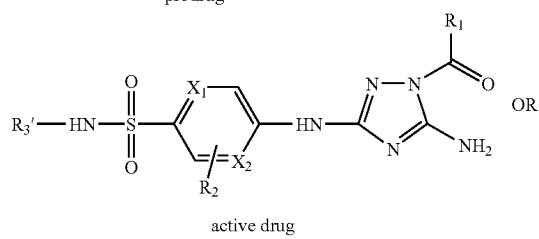

The synergistic action or enhancement of conventional chemotherapeutic agent by a test compound can also be determined with this model by comparing animals treated with the standard therapy alone to animals treated with test compound plus the same standard therapy. An additive effect on the delay of tumor growth will be observed if synergistic action due to test compound is occurring.

While the foregoing specification teaches the principles of the present invention, with examples provided for the purpose of illustration, it will be understood that the practice of the invention encompasses all of the usual variations, adaptations and modifications.

Throughout this application, various publications are cited. The disclosure of these publications is hereby incorporated by reference into this application to describe more fully the state of the art to which this invention pertains.

What is claimed is:

1. A compound of formula I:

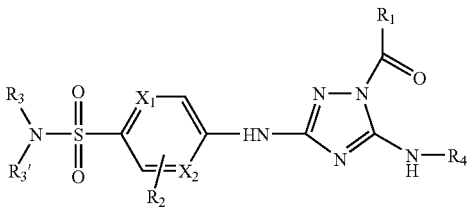

wherein:

$X_1$ and $X_2$ are independently selected from CH and N;

$R_1$ is selected from the group consisting of a carbocyclic, a heteroaryl, and a heterocyclic, and wherein $R_1$ is optionally substituted with one or more substitutents independently selected from the group consisting of amido, phosphonato, phosphine, carboxyl, thiocarbonyl, sulfonyl, nitro, thiol, thioether, amine, cyano, N—($C_{1-6}$-alkyl)amino, N,N—($C_{1-6}$-alkyl)$_2$amino, sulfonamide, ketone, aldehyde, ester, halogen, oxygen, haloalkyl, $C_{1-6}$-alkyl, $C_{2-6}$-alkenyl, $C_{2-6}$-alkynyl, hydroxyl and $C_{1-6}$-alkoxyl;

$R_2$ is selected from the group consisting of hydrogen, hydroxy, nitro, amino, carboxy, carbamoyl, halo, cyano, trifluoromethyl, trifluoromethoxy, sulphamoyl, mercapto, $C_{1-6}$-alkyl, $C_{2-6}$-alkenyl, $C_{2-6}$-alkynyl, $C_{1-6}$-alkoxyl, N—($C_{1-6}$-alkyl)amino, N,N—($C_{1-6}$-alkyl)$_2$amino, and sulfonyl;

$R_3$ and $R_4$ are independently selected from the group consisting of hydrogen, —$CH_2OPO_3R_5R_6$, —$CH_2OCOR_7$, —$CH_2OCO_2R_7$, —$CH_2OCONHR_7$, —$COR_7$, wherein $R_3$ and $R_4$ are not simultaneously hydrogen;

$R_3'$ is selected from the group consisting of hydrogen, heterocyclic and $C_{1-8}$alkyl, wherein $C_{1-8}$alkyl is optionally substituted with one or more of —$CO_2H$, —$CO_2$($C_{1-6}$)alkyl, hydroxy, $C_{1-6}$alkoxy, amino, aminoacylamino, N—($C_{1-6}$-alkyl)amino, N,N—($C_{1-6}$alkyl)$_2$ amino, heterocyclic or heteroaryl;

$R_5$ and $R_6$ are each selected from the group consisting of hydrogen, $C_{1-6}$alkyl, Na, K and $NH_4$ and are the same unless either $R_5$ or $R_6$ is absent, hydrogen or $C_{1-6}$alkyl, in which case the other is different, or alternatively, $R_5$ and $R_6$ together represent calcium or magnesium;

$R_7$ is heterocyclic or $C_{1-6}$alkyl, wherein $C_{1-6}$alkyl is optionally substituted with one or, more of —$CO_2H$, —$CO_2$($C_{1-6}$)alkyl, amino, amino-$COR_8$, carbamoyl, carbamoyl($C_{1-6}$)alkyl, guanidino, mercapto, thio($C_{1-6}$)alkyl, hydroxy, N—($C_{1-6}$-alkyl)amino, N,N—($C_{1-6}$-alkyl)$_2$ amino, aryl optionally substituted on aryl with one or more of $C_{1-4}$alkyl, $C_{1-4}$alkoxy, hydroxy, halogen, amino, aminoalkyl, nitro or cyano, heterocyclic, —$(OCH_2CH_2)_nOCH_3$ where n is 0-400, —$(OCH_2CH_2)_n$ OH where n is 0-400, or —$(OCH_2CH_2)_nOCH_2CO_2H$ where n is 0-400; and R8 is $C_{1-6}$alkyl optionally substituted with one or more of —$CO_2H$, —$CO_2$($C_{1-6}$)alkyl, amino, aminoacylamino, carbamoyl, carbamoyl($C_{1-6}$)alkyl, guanidino, mercapto, thio($C_{1-6}$)alkyl, hydroxy, N—($C_{1-6}$-alkyl)amino, N,N—($C_{1-6}$-alkyl)$_2$amino, aryl optionally substituted on aryl with one or more of $C_{1-4}$-alkyl, $C_{1-4}$alkoxy, hydroxy, halogen, amino, aminoalkyl, nitro or cyano, heterocyclic, —$(OCH_2CH_2)_nOCH_3$ where n is 0-400, —$(OCH_2CH_2)_nOH$ where n is 0-400, or —$(OCH_2CH_2)_n OCH_2CO_2H$ where n is 0-400;

or a pharmaceutically acceptable salt thereof.

2. The compound according to claim 1, wherein $R_4$ is hydrogen.

3. The compound according to claim 1, wherein $R_3$ is —$COR_7$.

4. The compound according to claim 1, wherein $X_1$ and $X_2$ are each CH.

5. The compound according to claim 1, wherein $R_1$ is a carbocyclic compound selected from cyclopropyl, cyclobutyl, cyclopentyl, cyclohexyl, phenyl or naphthyl each optionally substituted with one or more of amido, phosphonato, phosphine, carboxyl, thiocarbonyl, sulfonyl, nitro, thiol, thioether, amine, cyano, N—($C_{1-6}$-alkyl)amino, N,N—($C_{1-6}$-alkyl)$_2$amino, sulfonamide, ketone, aldehyde, ester, halogen, oxygen, haloalkyl, $C_{1-6}$-alkyl, $C_{2-6}$-alkenyl, $C_{2-6}$-alkynyl, hydroxyl or $C_{1-6}$-alkoxyl.

6. The compound according to claim 1, wherein $R_1$ is phenyl optionally substituted with one or more of amido, phosphonato, phosphine, carboxyl, thiocarbonyl, sulfonyl, nitro, thiol, thioether, amine, cyano, N—($C_{1-6}$-alkyl)amino, N,N—($C_{1-6}$-alkyl)$_2$amino, sulfonamide, ketone, aldehyde, ester, halogen, oxygen, haloalkyl, $C_{1-6}$-alkyl, $C_{2-6}$-alkenyl, $C_{2-6}$-alkynyl, hydroxyl or $C_{1-6}$-alkoxyl.

7. The compound according to claim 1, wherein $R_1$ is phenyl optionally substituted with one or more of halogen.

8. The compound according to claim 1, wherein $R_1$ is a heterocyclic compound selected from pyrrolidinyl, piperidinyl or piperazinyl each optionally substituted with one or more of amido, phosphonato, phosphine, carboxyl, thiocarbonyl, sulfonyl, nitro, thiol, thioether, amine, cyano, N—($C_{1-6}$- alkyl)amino, N,N—($C_{1-6}$-alkyl)$_2$amino, sulfonamide, ketone, aldehyde, ester, halogen, oxygen, haloalkyl, $C_{1-6}$-alkenyl, $C_{2-6}$-alkynyl, hydroxyl or $C_{1-6}$-alkoxyl.

9. The compound according to claim 1, wherein $R_1$ is a heteroaryl compound selected from pyrazolyl, pyridinyl, pyrazinyl, pyridazinyl, pyrimidinyl, morpholinyl, thiazinyl, oxazinyl, pyrrolyl, indolyl, furanyl, thiophenyl, imidazolyl, oxazolyl, isoxazolyl, thiazolyl, triazolyl, tetrazolyl, quinolinyl, isoquinolinyl, quinazolinyl, acridinyl, benzimidazolyl, benzothiophenyl or benzofuranyl each optionally substituted with one or more of amido, phosphonato, phosphine, carboxyl, thiocarbonyl, sulfonyl, nitro, thiol, thioether, amine, cyano, N—($C_{1-6}$-alkyl)amino, N,N—($C_{1-6}$-alkyl)$_2$amino, sulfonamide, ketone, aldehyde, ester, halogen, oxygen, haloalkyl, $C_{1-6}$-alkyl, $C_{2-6}$-alkenyl, $C_{2-6}$-alkynyl, hydroxyl or $C_{1-6}$-alkoxyl.

10. The compound according to claim 1, wherein $R_2$ is hydrogen.

11. The compound according to claim 1, wherein $R_3$ and $R_4$ are independently selected from hydrogen or —$COR_7$, wherein $R_3$ and $R_4$ are not simultaneously hydrogen.

12. The compound according to claim 1, wherein $R_3'$ is a heterocyclic compound selected from morpholinyl, tetrazolyl, pyrrolidinyl, piperidinyl, piperazinyl or 4-methyl-piperazin-1-yl.

13. The compound according to claim 1, wherein $R_3'$ is a heteroaryl compound selected from imidazolyl, 2-methyl-imidazolyl, 2,3-dimethyl-imidazolyl, 1,2,3-triazolyl or 1,2,4-triazolyl.

14. The compound according to claim 1, wherein $R_3'$ is hydrogen.

15. The compound according to claim 1, wherein $R_7$ is a heterocyclic compound selected from morpholinyl, tetrazolyl, pyrrolidinyl, piperidinyl, piperazinyl or 4-methyl-piperazin-1-yl.

16. The compound according to claim 1, wherein $R_7$ is heterocyclic or $C_{1-6}$alkyl, wherein $C_{1-6}$alkyl is optionally substituted with one or more of —$CO_2H$, —$CO_2(C_{1-6})$alkyl, amino, amino-$COR_8$, carbamoyl, carbamoyl($C_{1-6}$)alkyl, guanidino, mercapto, thio($C_{1-6}$)alkyl, hydroxy, N,N—($C_{1-6}$-alkyl)$_2$amino, phenyl optionally substituted on phenyl with one or more of $C_{1-4}$alkyl, $C_{1-4}$alkoxy, hydroxy, halogen, amino, aminoalkyl, nitro or cyano, heterocyclic, —($OCH_2CH_2)_n OCH_3$ where n is 0, 1, 2 or 3, —($OCH_2CH_2)_n OH$ where n is 0, 1, 2 or 3, or —($OCH_2CH_2)_n OCH_2CO_2H$ where n is 0, 1, 2 or 3.

17. The compound according to claim 1, wherein $R_7$ is heterocyclic or $C_{1-6}$alkyl, wherein $C_{1-6}$alkyl is optionally substituted with one or more of —$CO_2H$, —$CO_2(C_{1-6})$alkyl, amino, amino-$COR_8$, carbamoyl, carbamoyl($C_{1-6}$)alkyl, guanidino, mercapto, thio($C_{1-6}$)alkyl, hydroxy, N,N—($C_{1-6}$-alkyl)$_2$amino, phenyl optionally substituted on phenyl with one or more of hydroxy, heterocyclic, —($OCH_2CH_2)_n OCH_3$ where n is 1 or 2 or —($OCH_2CH_2)_n OCH_2CO_2H$ where n is 1 or 2.

18. The compound according to claim 1, wherein $R_7$ is heterocyclic or $C_{1-6}$alkyl, wherein $C_{1-6}$alkyl is optionally substituted with one or more of —$CO_2H$, —$CO_2(C_{1-6})$alkyl, amino, amino-$COR_8$, hydroxy, N,N—($C_{1-6}$-alkyl)$_2$amino, heterocyclic, —($OCH_2CH_2)_n OCH_3$ where n is 1 or 2 or —($OCH_2CH_2)_n OCH_2CO_2H$ where n is 1 or 2.

19. The compound according to claim 1, wherein $R_8$ is $C_{1-6}$alkyl optionally substituted with one or more of —$CO_2H$, —$CO_2(C_{1-6})$alkyl, amino, hydroxy, N—($C_{1-6}$-alkyl)amino, N,N—($C_{1-6}$-alkyl)$_2$amino, aryl optionally substituted on aryl with one or more of $C_{1-4}$alkyl, $C_{1-4}$alkoxy, hydroxy, halogen, amino or aminoalkyl, heterocyclic, —($OCH_2CH_2)_n OCH_3$ where n is 0, 1, 2 or 3, —($OCH_2CH_2)_n OH$ where n is 0, 1, 2 or 3, or —($OCH_2CH_2)_n OCH_2CO_2H$ where n is 0, 1, 2 or 3.

20. The compound according to claim 1, wherein $R_8$ is $C_{1-6}$alkyl optionally substituted with one or more of amino.

21. A compound selected from the group consisting of:

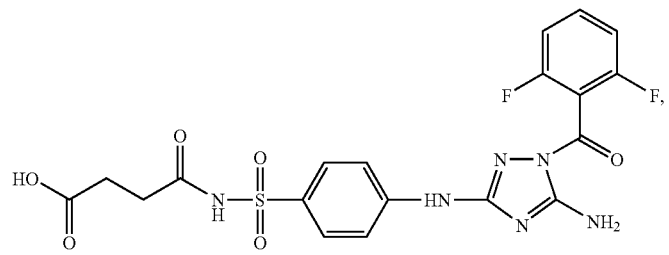

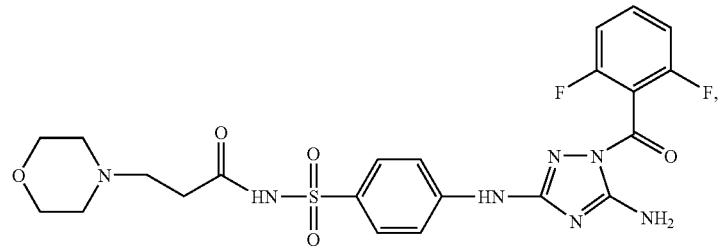

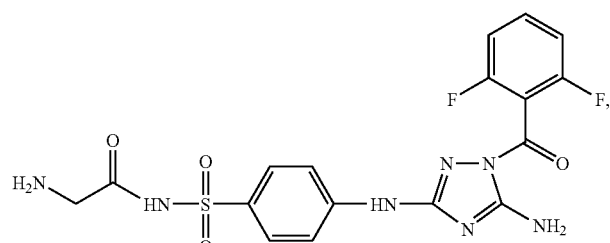

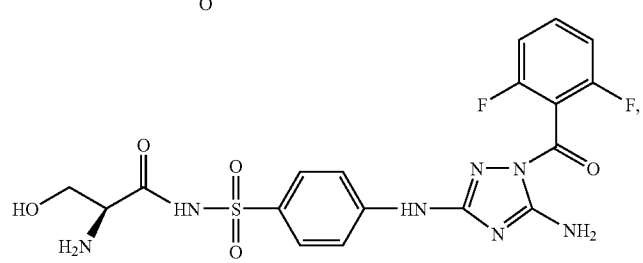

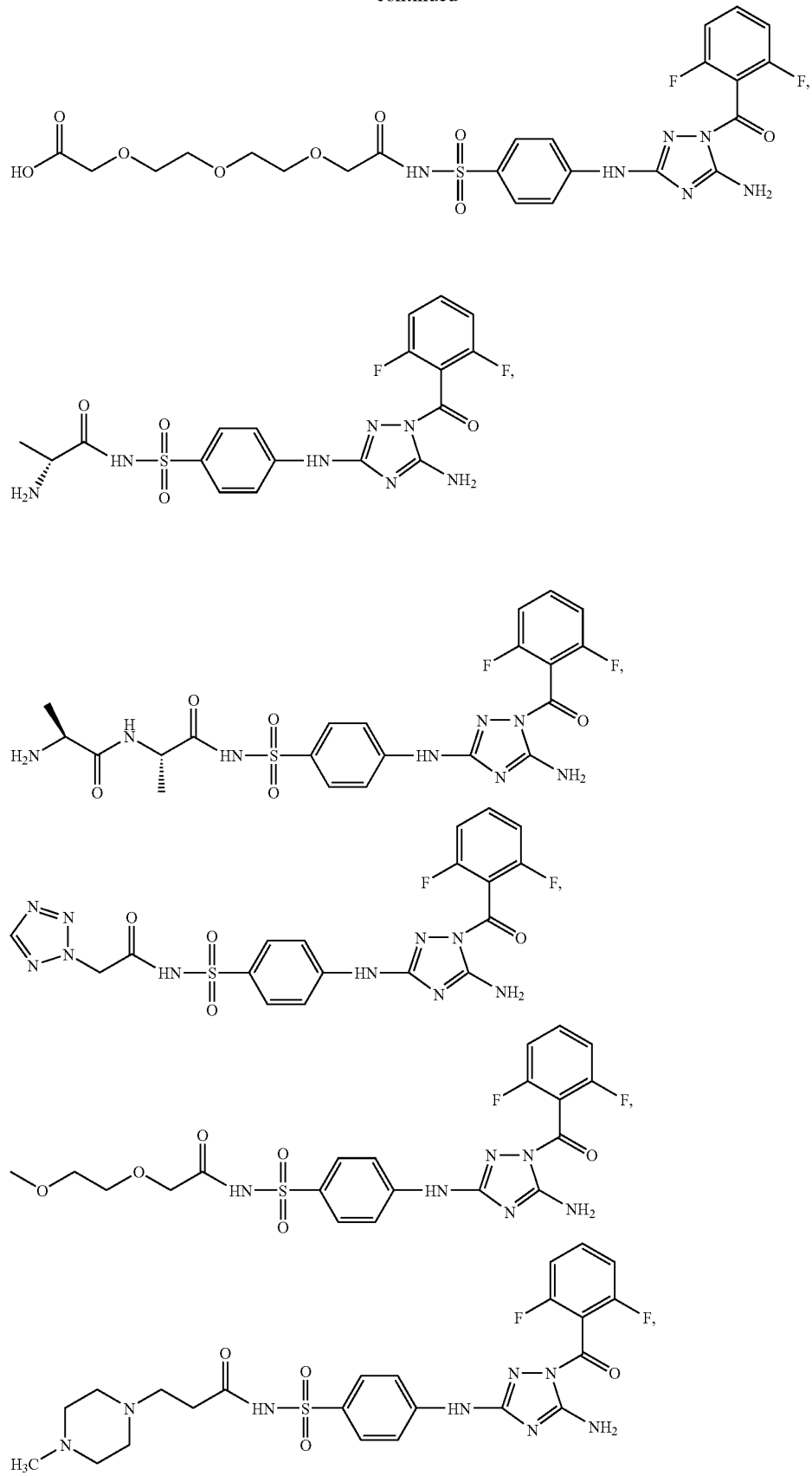

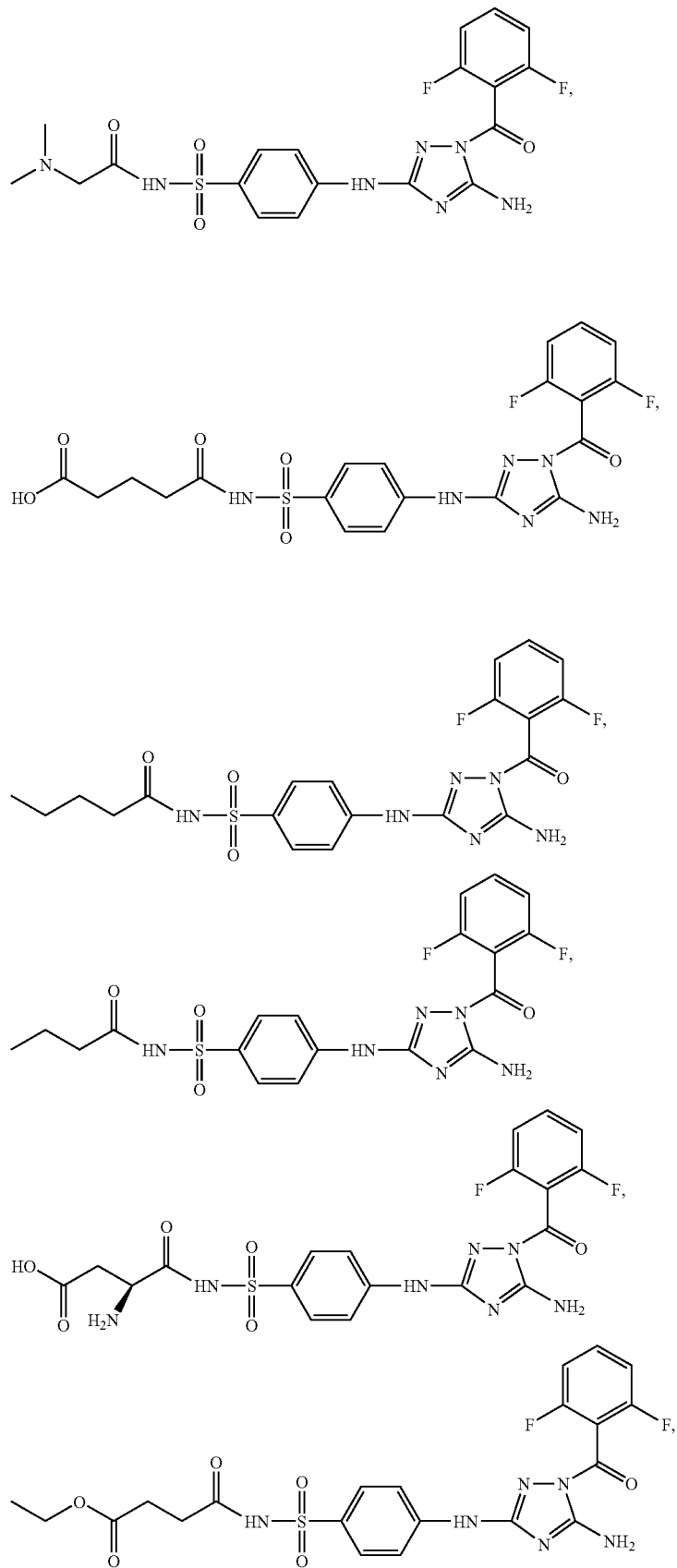

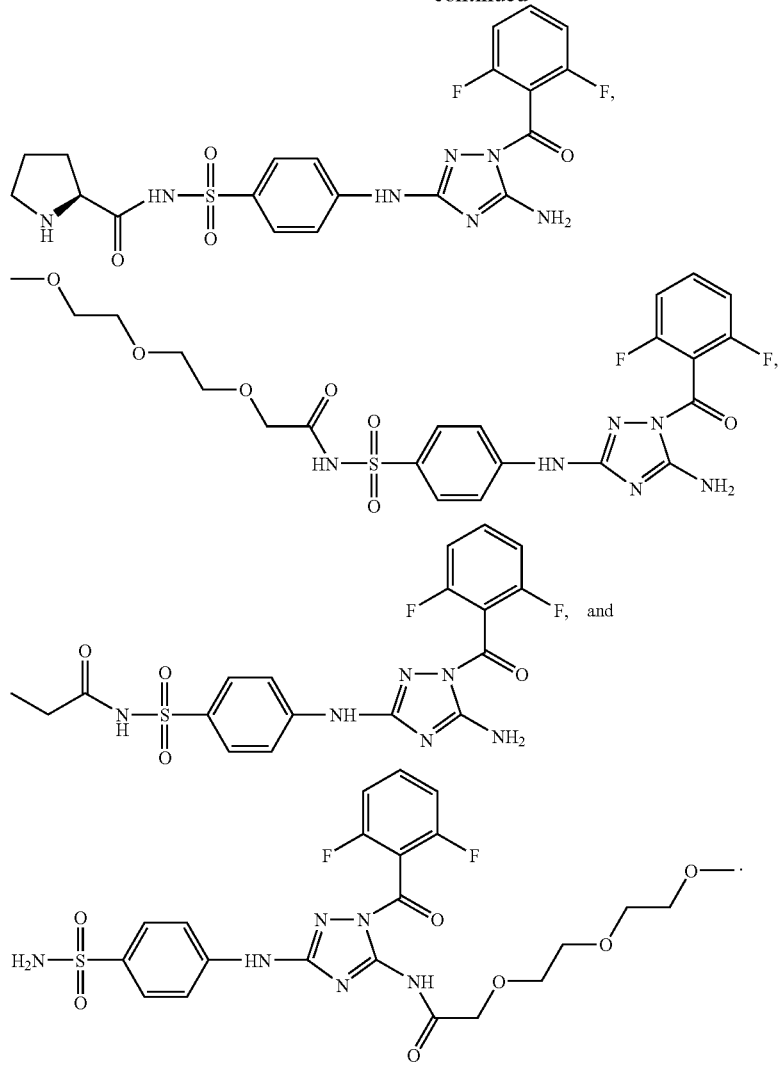

22. The compound of claim 1, wherein the compound is an isolated form thereof.

23. A pharmaceutical composition comprising an effective amount of a compound of claim 1 and a pharmaceutically acceptable carrier.

24. A pharmaceutical composition comprising (a) an effective amount of a compound of claim 1, and (b) a pharmaceutically acceptable carrier, diluents, or vehicle therefore.

25. The pharmaceutical composition of claim 24, wherein the effective amount of the compound is in a range of from about 0.001 mg/kg to about 300 mg/kg of body weight per day.

26. A process for preparing a pharmaceutical composition comprising the step of admixing a compound of claim 1 and a pharmaceutically acceptable carrier.

27. A process for preparing a compound of claim 1 comprising the steps of a. reacting a compound of Formula A1 with a compound of Formula A2 to prepare a compound of Formula A3;

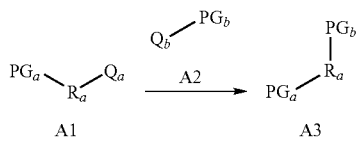

wherein the Formula A1 compound comprises a $PG_a$ suitable protecting group portion, a $R_a$ suitable linking group portion and a $Q_a$ suitable reaction group portion;

wherein the Formula A2 compound comprises a $Q_b$ suitable reaction group portion and a $PG_b$ suitable protecting group portion;

wherein the Formula A3 compound comprises a $PG_a$ suitable protecting group portion, a $R_a$ suitable linking group portion and a $Q_a$ suitable reaction group portion;

wherein the $R_a$ linking group further incorporates certain portions of the $Q_a$ and $Q_b$ reaction groups as a product of the reaction;

b. transforming a compound of Formula A3 into a compound of Formula A4;

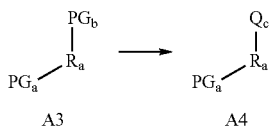

wherein the Formula A4 compound comprises a $PG_a$ suitable protecting group portion, a $R_a$ suitable linking group portion and a $Q_c$ suitable reaction group portion;

c. reacting a compound of Formula A5 with a compound of Formula A4 to prepare a compound of Formula A6;

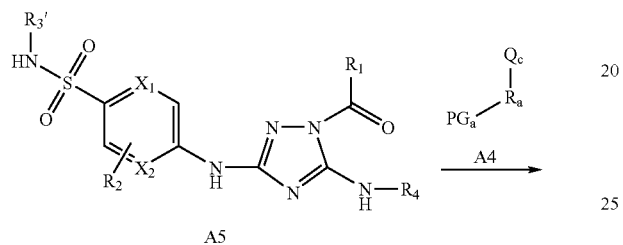

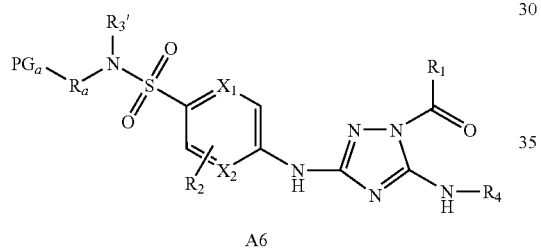

d. transforming a compound of Formula A6 into a compound of Formula (I),

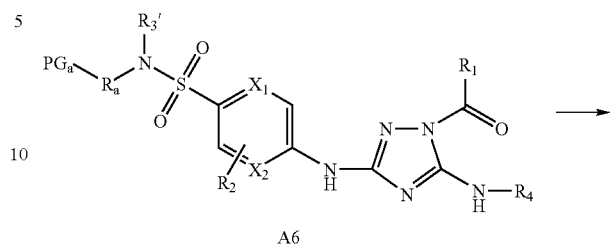

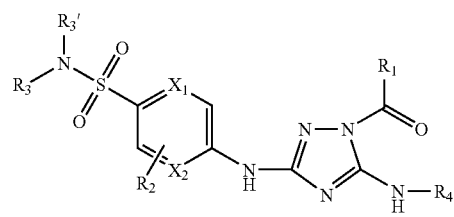

wherein the Formula (I) compound $R_3$ group incorporates certain portions of the $R_a$ linking group as a product of the reaction.

* * * * *